US011459592B2

(12) United States Patent
Davidovich et al.

(10) Patent No.: US 11,459,592 B2
(45) Date of Patent: Oct. 4, 2022

(54) PROCESSES FOR THE PRODUCTION OF CANNABINOIDS FROM A CARBON SOURCE PRECURSOR

(71) Applicant: SYNTIVA THERAPEUTICS, INC., Baltimore, MD (US)

(72) Inventors: Adam Davidovich, Baltimore, MD (US); Brian Chan, Allen, TX (US); Neil Gupta, Prospect, KY (US); Alim Ladha, Oakville (CA)

(73) Assignee: SYNTIVA THERAPEUTICS, INC., Baltimore, MD (US)

( * ) Notice: Subject to any disclaimer, the term of this patent is extended or adjusted under 35 U.S.C. 154(b) by 80 days.

(21) Appl. No.: 17/067,921

(22) Filed: Oct. 12, 2020

(65) Prior Publication Data
US 2021/0024968 A1 Jan. 28, 2021

Related U.S. Application Data

(62) Division of application No. 16/442,066, filed on Jun. 14, 2019, now Pat. No. 10,801,049.

(60) Provisional application No. 62/685,006, filed on Jun. 14, 2018.

(51) Int. Cl.
C12P 17/06 (2006.01)
C12N 15/70 (2006.01)
A61K 31/352 (2006.01)
C12N 1/20 (2006.01)
C12N 15/52 (2006.01)

(52) U.S. Cl.
CPC ............ C12P 17/06 (2013.01); A61K 31/352 (2013.01); C12N 1/20 (2013.01); C12N 15/52 (2013.01); C12N 15/70 (2013.01); C12Y 101/01088 (2013.01); C12Y 121/03007 (2015.07); C12Y 203/01009 (2013.01); C12Y 203/0301 (2013.01); C12Y 205/01102 (2015.07); C12Y 207/01036 (2013.01); C12Y 207/04002 (2013.01); C12Y 207/06005 (2013.01); C12Y 401/01033 (2013.01); C12Y 602/01001 (2013.01); C12Y 604/01002 (2013.01)

(58) Field of Classification Search
None
See application file for complete search history.

(56) References Cited

U.S. PATENT DOCUMENTS

| 8,859,277 B2 | 10/2014 | Court et al. |
| 8,884,100 B2 | 11/2014 | Page et al. |
| 8,927,241 B2 | 1/2015 | Ajikumar et al. |
| 9,359,624 B2 | 6/2016 | Ajikumar et al. |
| 9,376,367 B2 | 6/2016 | Herkenroth et al. |
| 9,526,715 B1 | 12/2016 | Winnicki et al. |
| 9,587,212 B2 | 3/2017 | Winnicki et al. |
| 9,809,804 B2 | 11/2017 | Garg et al. |
| 9,822,384 B2 | 11/2017 | Poulos et al. |
| 9,937,219 B2 | 4/2018 | Raderman |
| 9,951,345 B2 | 4/2018 | Steen et al. |
| 10,059,971 B2 | 8/2018 | Page et al. |
| 10,093,949 B2 | 10/2018 | Poulos et al. |
| 2017/0016034 A1 | 1/2017 | Haushalter et al. |
| 2018/0371507 A1 | 12/2018 | Poulos et al. |
| 2019/0169661 A1 | 6/2019 | Page et al. |
| 2019/0300888 A1 | 10/2019 | Keasling et al. |

FOREIGN PATENT DOCUMENTS

WO 2016010827 A1 1/2016

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Tyler J. Ford, et al., "Enhancement of E. coli acyl-CoA synthetase FadD activity on medium chain fatty acids", Jun. 30, 2015, 18 pages.
"The Huge (or Tiny) Ecological Footprint of Cannabis", www.footprintnetwork.org, Aug. 16, 2017 (5 pages).
Evan Mills, "The carbon footprint of indoor Cannabis production", Energy Policy, Apr. 17, 2012, 10 pages.
Jorge Alonso-Gutierrez, et al., "Metabolic engineering of Escherichia coli for limonene and perillyl alcohol production", Metabolic Engineering, May 29, 2013, 9 pages.
Xiaozhou Luo, et al., "Complete biosynthesis of cannabinoids and their unnatural analogues in yeast", Nature, Feb. 27, 2019, 18 pages.
Kristala L. Jones Prather et al., "De novo biosynthetic pathways: rational design of microbial chemical factories",19 Current Opinion in Biotechnology 468-74; Sep. 5, 2008.
Accession B1Q2B6, May 20, 2008.
Accession I6WU39, Oct. 3, 2012.
Accession AYN80748, Mar. 17, 2011.

(Continued)

Primary Examiner — Christian L Fronda
(74) Attorney, Agent, or Firm — Ware, Fressola, Maguire & Barber LLP

(57) ABSTRACT

A method is provided for biosynthetic production of cannabinoids in microorganisms from a carbon source precursor. This method describes the genetic modifications needed to engineer microorganisms to produce cannabinoids as well as a method for identifying and quantifying cannabinoids from fermentation broth. A system is also provided for tuning the method to produce different cannabinoids of interest by systematically modulating the enzymes encoded by the genetic modifications introduced in the microorganism.

10 Claims, 5 Drawing Sheets
Specification includes a Sequence Listing.

(56) References Cited

OTHER PUBLICATIONS

Lance Kizer et al., "Application of Functional Genomics to Pathway Optimization for Increased Isoprenoid Production," 74 Applied and Environmental Microbiology 3229-3241, May 2008.

Angela Carvalho et al., "Designing microorganisms for heterologous biosynthesis of cannabinoids," 17 FEMS Yeast Research, Jun. 4, 2017.

Roberto A Chica et al., "Semi-rational approaches to engineering enzyme activity: combining the benefits of directed evolution and rational design," 16 Current Opinion in Biotechnology 378-384, Jul. 1, 2005.

Kevin V. Solomon et al., "A dynamic metabolite valve for the control of central carbon metabolism", 14 Metabolic Engineering 661-671, Sep. 28, 2012.

Raushan Kumar Singh et al., "Protein Engineering Approaches in the Post-Genomic Era," 18 Current Protein and Peptide Science, 2017.

\* cited by examiner

PROCESSES FOR THE PRODUCTION OF CANNABINOIDS FROM A CARBON SOURCE PRECURSOR

CROSS-REFERENCE TO RELATED APPLICATIONS

The present application is a divisional application of U.S. application Ser. No. 16/442,066 filed on Jun. 14, 2019 and issued as U.S. Pat. No. 10,801,049 on Oct. 13, 2020, which claims the benefit of U.S. Provisional Patent Application No. 62/685,006 filed Jun. 14, 2018, both of which are hereby incorporated by reference in their entireties.

BACKGROUND OF THE INVENTION

1. Field of Invention

This invention relates to cannabinoid compounds and their production. Further, the invention relates generally to the fields of metabolic engineering and chemical quantification. Specifically, this invention relates to the use of metabolic engineering techniques to manipulate microorganisms to produce cannabinoids and chemical techniques to quantify said production.

Cannabinoids are a class of over 100 compounds that are naturally produced in the Cannabis sativa ("C. sativa") plant. Certain cannabinoids bind to cannabinoid receptors in the human body that affect neurotransmitter release. Further, some cannabinoids are implicated in the treatment of many diseases. For example, tetrahydrocannabinol (THC) is FDA-approved to treat nausea and vomiting resulting from chemotherapy as well as wasting and appetite loss resulting from HIV/AIDS medications. THC is also reportedly beneficial as a therapy for chronic pain, spasticity due to multiple sclerosis, and anxiety disorder. Further, combined cannabinoid therapies (ex. THC/Cannabidiol (CBD)) have the possibility to improve THC treatment and even treat separate indications.

2. Description of the Related Art

Current methods of cannabinoid production for pharmaceutical purposes include extraction from plants and chemical synthesis. Crude Cannabis plant material is inherently variable in cannabinoid composition, ultimately leading to variable purification efficacy for a given cannabinoid or mixture of cannabinoids. In the current pharmaceutical regulatory environment, it is challenging for drugs derived from crude Cannabis material to meet the FDA-required uniformity in quality and efficacy.

In addition, the current manufacturing process is expensive and energy inefficient. Estimates by the Global Footprint Network place the ecological footprint of producing a single kilogram of dried Cannabis per year at 3,700 square meters of biologically productive space. "The Huge (or Tiny) Ecological Footprint of Cannabis," Global Footprint Network, Aug. 28, 2017. Furthermore, 4.6 tons of carbon dioxide emissions, or the equivalent of 3 million cars in the US per year, are from Cannabis production. Id. Estimates put the actual energy cost of marijuana production in the US at $6 billion per year. Mills, Evan. "The Carbon Footprint of Indoor Cannabis Production." Energy Policy 46 (2012): 58-67. As Cannabis production scales to meet growing demand, the ecological impact will only worsen.

Thus, a more standardized approach to cannabinoid production must be explored for THC and cannabinoid therapies to reach their potential. As such, this invention demonstrates the cheap, easily scalable, and highly tunable biosynthetic production of cannabinoids in microorganisms. Further, this invention provides methods to quantify said production.

SUMMARY OF THE INVENTION

An aspect of this invention relates to genetically modified microorganisms that produce cannabinoids. The genetic modifications include the transformation of certain DNA sequences that encode (1) the enzymes necessary for production of hexanoyl-CoA from hexanoate and/or glucose (which is converted to hexanoate), (2) olivetol synthase and olivetolic acid cyclase to produce olivetolate (OA) from hexanoyl-CoA, (3) the enzymes necessary to produce geranyl pyrophosphate ("GPP"), (4) CsPT1 to produce cannabigerolic acid ("CBGA") from olivetolate and GPP, and (5) an enzyme that catalyzes the production of another cannabinoid with CBGA as a precursor, such as the enzyme tetrahydrocannabinolic acid synthase, which catalyzes the production of tetrahydrocannabinolic acid ("THCA") from CBGA. The genetic modifications also include replacement of the FadD gene with a mutant copy which functions as a FadE knockout to minimize Hexanoyl-CoA degradation as well as the inclusion of a Glutathione-S-Transferase (GST) solubility tag and a thrombin cleavage site in the same open reading frame as the CsPT1 enzyme to increase protein expression.

Another aspect of this invention relates to the identification and quantification of cannabinoids from fermentation broth. This method comprises (1) solvent-solvent extraction of the cannabinoids with acetonitrile, (2) isolating broth from cells by centrifugation, (3) dilution of broth and lysing cells with acetonitrile, (4) heating cell pellets with acetonitrile, (5) running samples through an ultra-performance liquid chromatography (UPLC) system coupled with tandem mass spectrometry (MS/MS), and (6) comparing the obtained signal to standard curves obtained with internal standards of the desired cannabinoids.

The invention provides a cheaper method for cannabinoid production. It is also easily tailored to produce a wide variety of cannabinoids, by changing one or two of the DNA sequences transformed into the microorganisms. The following descriptions provide examples of the invention, though the invention is not limited by these examples.

A genetically modified micro-organism is provided that produces at least one cannabinoid from a carbon source precursor. In an embodiment of the invention, the microorganism is E. coli. In an embodiment, the genetically modified micro-organism is modified to express the one or more of the following thirteen enzymes: acetoacetyl-CoA synthase (AtoB), HMG-CoA synthase (HMGS), N-terminal truncated version of HMG-CoA reductase (HMGR), Mevalonate Kinase (MK), Phosphomevalonate Kinase (PMK), Phosphomevalonate Decarboxylase (PMD), isopentenyl diphosphate isomerase (IDI), Geranyl Pyrophosphate Synthase from Abies grandis which was codon optimized (co) for E. coli (trGPPS(co)), Olivetol Synthase (OLS), Olivetolic Acid Cyclase (OAC), Geranylpyrophosphate Olivetolate Geranyltransferase (CsPT1), and Glutathione S-transferases (GST).

In a further embodiment of the invention, the following FadD gene with V451A mutation was overexpressed and the FadE enzyme/gene was knocked out. Synthetic metabolic sspB-based protein degradation valves were recombineered into the following enzyme/genes: Phosphoglucose Isomerase (pgi), glucose 6-phosphate dehydrogenase (zwf), and Citrate Synthase (gltA) in their various combinations (pgi, zwf, gltA, pgi-zwf, pgi-gltA, zwf-gltA, pgi-zwf-gltA) by adding a C-terminal DAS+4 tag to each gene (SEQ ID NO. 12). This tag is the same for all three valves, although inserted into different places within the chromosome (overlapping sequences added to 5' region of this tag for specific integration).

In accordance with a further aspect of the invention, a vector is provided comprising DNA sequences encoding olivetol synthase (OLS) (SEQ ID NO. 1), olivetolic acid cyclase (OAC) (SEQ ID NO. 3), geranylpyrophosphate olivetolate geranyltransferase (CsPT1) (SEQ ID NO. 5), and glutathione S-transferases (GST) (SEQ ID NO. 7) with amino acid sequences SEQ ID NO. 2, SEQ ID NO. 4, SEQ ID NO. 6, and SEQ ID NO. 8, respectively, wherein the vector confers the ability to produce at least one cannabinoid from at least one carbon source.

In accordance with a further aspect of the invention, a method is provided to quantify at least one cannabinoid from fermentation broth.

In accordance with a further aspect of the invention, a process is provided to make a cannabinoid using a genetically modified micro-organism in accordance with any of the above-described embodiments.

In accordance with an aspect of the present invention, a method for producing at least one cannabinoid from a carbon source precursor is provided, the method comprising genetically modifying a bacterial strain to express enzymes for converting the carbon source precursor into the at least one cannabinoid within the genetically modified bacterial strain. In an embodiment of the method, the carbon source precursor is glucose and the method further comprises converting the glucose to hexanoate, and the at least one cannabinoid comprises cannabigerolic acid. In a further embodiment of the invention, the bacterial strain is $E.\ coli$. In certain embodiments of the method, genetically modifying the bacterial strain comprises recombinantly incorporating a mutated FadD gene to express a mutated FadD enzyme which knocks out a FadE gene of the bacterial strain, including wherein the mutated FadD gene comprises a nucleotide sequence of SEQ ID NO. 10. In further additional embodiments, genetically modifying the bacterial strain additionally or alternatively comprises transforming the bacterial strain to express olivetol synthase, olivetolic acid cyclase, and CsPT1, including wherein the olivetol synthase comprises a first amino acid sequence comprising the amino acid sequence of SEQ ID NO. 2, wherein the olivetolic acid cyclase comprises a second amino acid sequence comprising the amino acid sequence of SEQ ID NO. 4, and wherein the CSPT1 comprises a third amino acid sequence comprising the amino acid sequence of SEQ ID NO. 6. Transforming the bacterial strain may additionally or alternatively comprise transforming the bacterial strain with a plasmid having a nucleotide sequence comprising the nucleotide sequence of SEQ ID NO. 9. The plasmid comprises a nucleotide sequence for a Glutathione-S-Transferase (GST) solubility tag and a thrombin cleavage site in the same open reading frame as a nucleotide sequence for CsPT1. In further embodiments of the method, the method further comprises extracting the at least one cannabinoid produced by the genetically modified bacterial strain from a fermentation broth comprising the genetically modified bacterial strain.

In a further aspect of the invention, a genetically modified microorganism that produces at least one cannabinoid from a carbon source precursor is provided, wherein the microorganism is a bacterial strain genetically modified to express enzymes for converting the carbon source precursor into the at least one cannabinoid within the genetically modified bacterial strain. In certain embodiments, the bacterial strain is $E.\ coli$. The bacterial strain may comprise a recombinantly incorporated mutated FadD gene having the nucleotide sequence of SEQ ID NO. 10 to express a mutated FadD enzyme which knocks out a FadE gene of the bacterial strain. In additional or alternative embodiments, the microorganism is transformed with a plasmid to express olivetol synthase having a first amino acid sequence comprising amino acid sequence of SEQ ID NO. 2, olivetolic acid cyclase a second amino acid sequence comprising the amino acid sequence of SEQ ID NO. 4, and CsPT1 having a third amino acid sequence comprising the amino acid sequence of SEQ ID NO. 6. The plasmid comprises a nucleotide sequence comprising the nucleotide sequence of SEQ ID NO. 9. In further additional or alternative embodiments, the genetically modified microorganism comprises a first nucleotide sequence comprising the nucleotide sequence of SEQ ID NO. 9; a second nucleotide sequence comprising the nucleotide sequence of SEQ ID NO. 10; and a third nucleotide sequence comprising the nucleotide sequence of SEQ ID NO. 11. The genetically modified microorganism may further comprise recombineered metabolic protein degradation valves for one or more of a pgi gene, a zwf gene and a gltA gene.

In accordance with a further aspect of the invention, a plasmid is provided comprising the nucleotide sequence of SEQ ID NO. 9 that encodes olivetol synthase, olivetolic acid cyclase, and CsPT1. In a still further aspect of the invention, a vector comprising the aforementioned plasmid is provided.

DETAILED DESCRIPTION OF THE INVENTION

Figure 1:
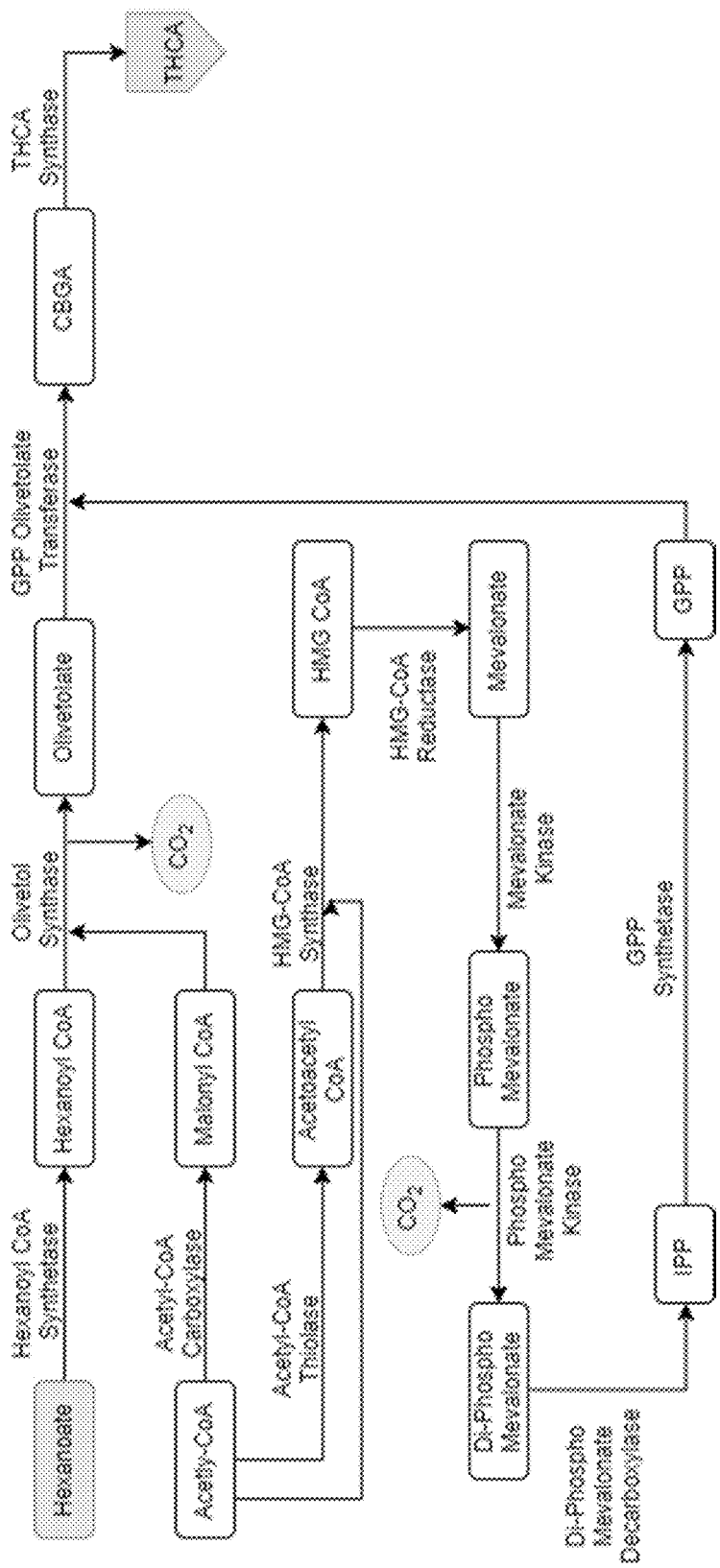
FIG. 1 shows the metabolic pathway of THCA production from hexanoate including the GPP pathway.

This example details the biosynthetic production of CBGA in $E.\ coli$ from glucose and quantifies the desired analyte with UPLC-MS/MS. Although this is a preferred embodiment of the invention, the invention is not limited to this sole example. Cannabinoids are naturally expressed in $C.\ sativa$, through a pathway partially depicted in FIG. 1. As such, the $C.\ sativa$ plant has genes that encode enzymes responsible for catalyzing cannabinoid production. This invention utilizes the $C.\ sativa$ genes that encode olivetol synthase, olivetolic acid cyclase, and CsPT1 which will convert hexanoyl CoA into olivetolate, produce olivetolic acid from olivetolate, and convert olivetolic acid into CBGA, respectively. Olivetolate and CBGA are precursors to many other cannabinoids, including cannabidiolate ("CBDA") and THCA.

The genetic sequence (from $C.\ sativa$, codon optimized for $E.\ coli$) of olivetol synthase according to the present application is incorporated in the Sequence Listings accompanying the present application as SEQ ID NO. 1, and the corresponding amino acid sequence for olivetol synthase encoded by SEQ ID NO. 1 is incorporated as SEQ ID NO. 2. The amino acid sequence of SEQ ID NO. 2, while encoded by SEQ ID NO. 1, substantially corresponds to the amino acid for olivetol synthase as expressed in *C. sativa*.

The genetic sequence (from *C. sativa*, codon optimized for *E. coli*) of olivetolic acid cyclase according to the present application is incorporated in the Sequence Listings accompanying the present application as SEQ ID NO. 3, and the corresponding amino acid sequence for olivetolic acid cyclase encoded by SEQ ID NO. 3 is incorporated as SEQ ID NO. 4. The amino acid sequence of SEQ ID NO. 4, while encoded by SEQ ID NO. 3, substantially corresponds to the amino acid for olivetolic acid cyclase as expressed in *C. sativa*.

The genetic sequence (from *C. sativa*, codon optimized for *E. coli*) of CsPT1 according to the present application is incorporated in the Sequence Listings accompanying the present application as SEQ ID NO. 5, and the corresponding amino acid sequence for CsPT1 encoded by SEQ ID NO. 5 is incorporated as SEQ ID NO. 6. The amino acid sequence of SEQ ID NO. 6, while encoded by SEQ ID NO. 5, substantially corresponds to the amino acid for CsPT1 as expressed in *C. sativa*.

The genetic sequence of the GST solubility tag and thrombin cleavage site, which is synthetic, according to the present application is incorporated in the Sequence Listings accompanying the present application as SEQ ID NO. 7, and the corresponding amino acid sequence is incorporated as SEQ ID NO. 8.

The genetic sequence for the modified plasmid incorporating genes that encode for olivetol synthase, olivetolic acid cyclase, and CsPT1 with GST solubility tag and thrombin cleavage site in the same open reading frame, according to the present application is incorporated in the Sequence Listings as SEQ ID NO. 9.

To manipulate *E. coli* to produce hexanoyl-CoA, a FadD mutant enzyme is recombinantly incorporated into the *E. coli* chromosome via the method described below. The genetic sequence of the FadD gene with V451A mutation as used in the present application is incorporated in the Sequences Listings as SEQ ID NO. 10.

The FadD enzyme converts hexanoate to hexanoyl-CoA, and the particular mutant (SEQ ID NO. 10) as used herein knocks out the fadE gene, which can degrade the desired hexanoyl-CoA. Further, an *E. coli* strain with recombineered metabolic valves for the pgi, zwf, and gltA genes was used. The nucleotide sequence of SEQ ID No. 12 was incorporated on to the C-terminal of each of these genes. The valves for the three genes decrease the citric acid cycle pathway, pentose phosphate production, and the glucose-6-phosphate isomerase when the cells are in production phase (no longer growing). These pathways and genes were identified by the COBRA Toolbox as candidates for downregulation in order to optimize flux of cannabinoids in the system.

Further, a mutated version of the pJBEI-6409 plasmid (SEQ ID NO. 11) is used to confer the ability to produce GPP and further convert this GPP into the more stable limonene in *E. coli*. This plasmid is derived from Alonso-Gutierrez J., Chan R, Batth T. S., et al., "Metabolic engineering of *Escherichia coli* for limonene and perillyl alcohol production," METAB ENG. 2013; 19:33-41. Limonene is produced as a product of GPP, and was included because of its easy identification by smell and UPLC. That is, presence of limonene indicates GPP production as well. *E. coli* cells with this plasmid are grown in shake flasks and production is induced as described below. After confirmation of GPP production, the *E. coli* cells are then transformed with a plasmid (SEQ ID NO. 9) according to the protocols below with the olivetol synthase (SEQ ID NO. 1), olivetolic acid cyclase (SEQ ID NO. 3), and CsPT1 (SEQ ID NO. 5) genes described previously (with the plasmid also including the GST solubility tag and thrombin cleavage site (SEQ ID NO. 7) in the open reading frame with the CsPT1 enzyme coding sequence. Cells are grown in shake flasks and production is induced as described below. A UPLC-MS/MS system is used to identify and quantify both olivetolate and CBGA.

Although the embodiments discussed herein describe the invention as applied to production of CBGA in *E. coli*, it should be noted that other embodiments can use different microorganisms other than *E. coli*, and can produce other cannabinoids via transformation of different *C. sativa* genes. Different UPLC-MS/MS systems could be used as well. Those skilled in the art should understand that even though these changes and other variations can be used to produce other cannabinoids in other microorganisms, the methods still adhere to this invention. As such, the following examples describe the breadth of this invention,

EXAMPLES

Example 1

Production of CBGA in *E. coli* from Glucose

*E. coli* cells were engineered to contain metabolic valves for the pgi, zwf, and gltA genes as described above. Further, the FadD mutant enzyme (SEQ ID NO. 10) was recombinantly expressed within the cells. The modified pBbA5c-MevT(CO)-T1-MBIS(CO, ispA) plasmid (SEQ ID NO. 11) was transformed into the cells. The cells were grown and production was induced as described below. The cells and broth were separated by centrifugation. The broth was then diluted 1:1 with acetonitrile.

Figure 2:
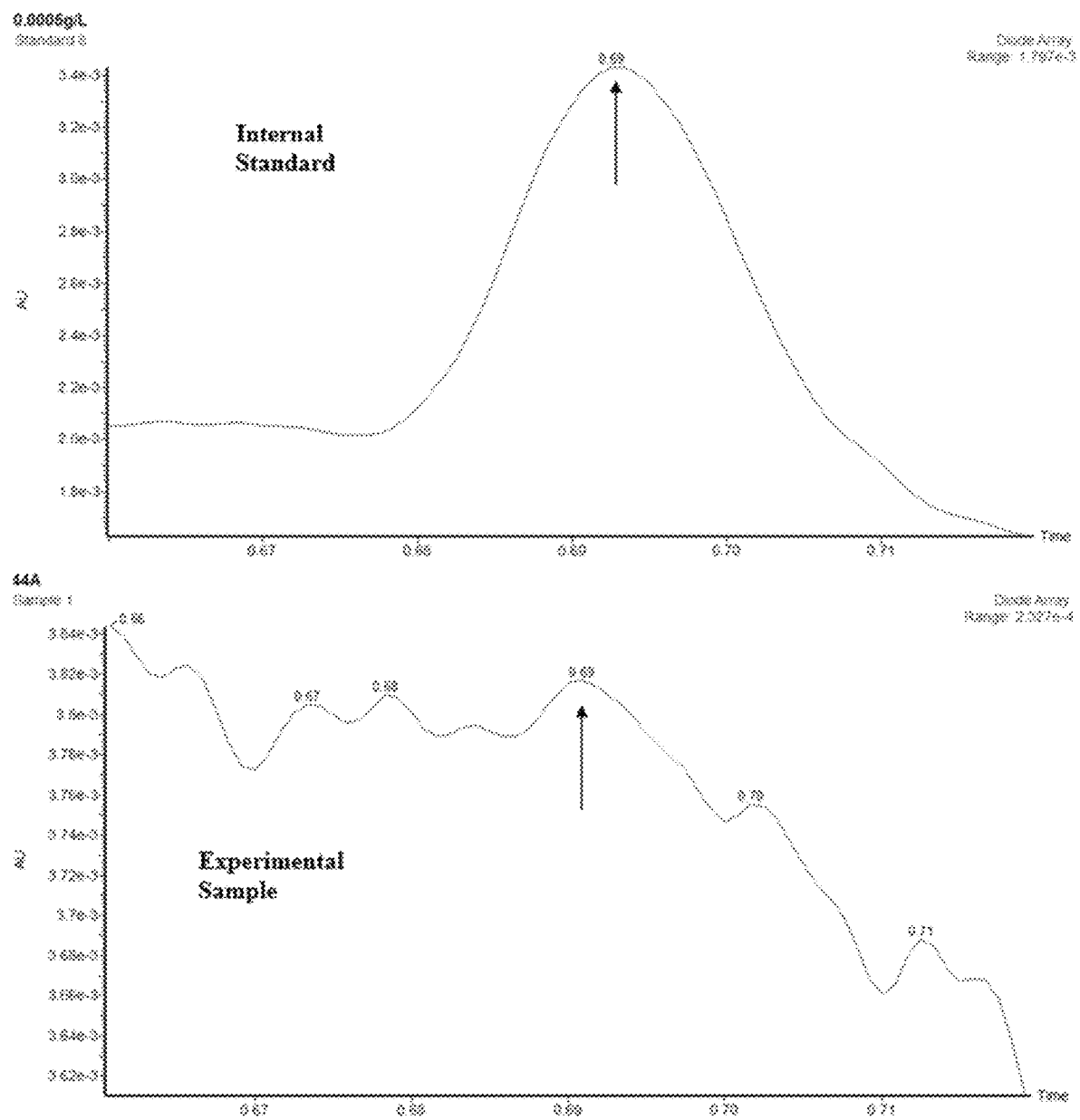
FIG. 2 shows experimental data from UPLC-UV/Vis identification of limonene.

A UPLC-UV/Vis (Waters Acquity) system was used to identify and quantify limonene. Chromatography was performed with a Waters Acquity UPLC system on a Restek ARC Raptor C18 column (50 mm length with 1.8 μm particles). The column was maintained at a temperature of 85° C. The mobile phase was 5 mM ammonium formate in acetonitrile, adjusted to a pH of 4.5. Flow rate was 0.75 mL/min, and the injection volume was 10 μL. Each injection had a run time of 4 minutes. Chromatograms for successful production of limonene are shown in FIG. 2. Note the peak at 0.69 seconds in both the internal standard and the experimental chromatograms.

Figure 3:
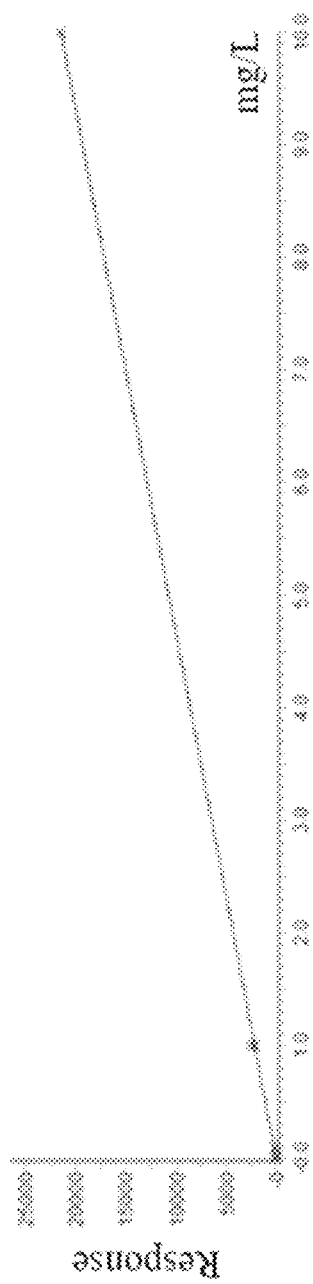
FIG. 3 shows standard curves for olivetolate and CBGA.
Figure 3:
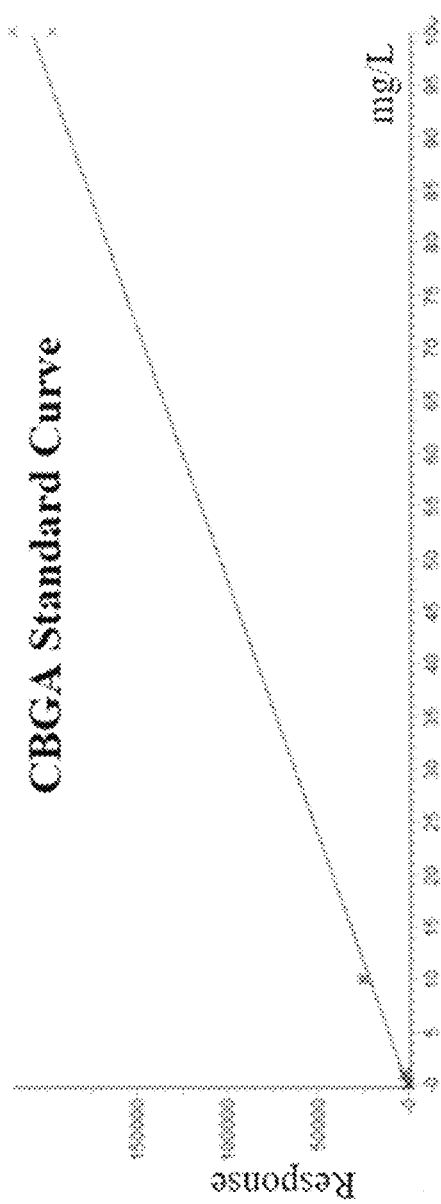
Figure 4:
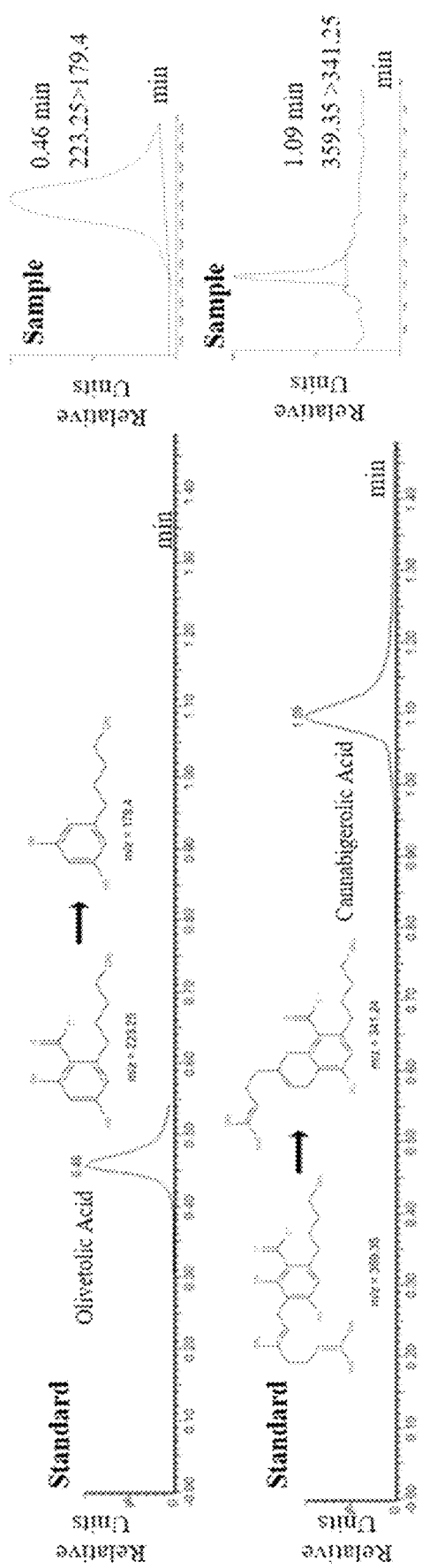
FIG. 4 shows internal standard and experimental data from UPLC-MS/MS identification and quantification of olivetolate and CBGA.

The genes for olivetol synthase (SEQ ID NO. 1), olivetolic acid cyclase (SEQ ID NO. 3), and CsPT1 (SEQ ID NO. 5) (including the GST solubility tag and thrombin cleavage site (SEQ ID NO. 7)) were then transformed into the cells via a plasmid (SEQ ID NO. 9). Cells were grown, and production was induced as described below. The cells and broth were separated by centrifugation, and the broth was diluted 1:1 with acetonitrile. A UPLC-MS/MS system was used to identify and quantify both olivetolate and limonene as described in the methods below. FIG. 3 shows the standard curves used for method calibration. FIG. 4 shows successful production of olivetolate and CBGA. The experimental peaks for olivetolate and CBGA at 0.46 and 1.09 min with m/z transitions of 223.25 to 179.4 and 359.35 to 341.24, respectively, match those for the standard peaks.

Example 2

Production of Cannabinoids from a Carbon Sugar Precursor in Yeast

A preferred embodiment of this invention uses *E. coli* as the target microorganism. However, yeast can just as easily be used. The same genes transformed into *E. coli* will be transformed into *Saccharomyces cerivisiae*. The *S. cerivisiae* will grow and production will be induced in the similar manner as *E. coli* but utilizing different promoters optimized for *S. cerivisiae*.

Example 3

Production of Cannabidiolate (CBDA) and Other Cannabinoids

Figure 5:
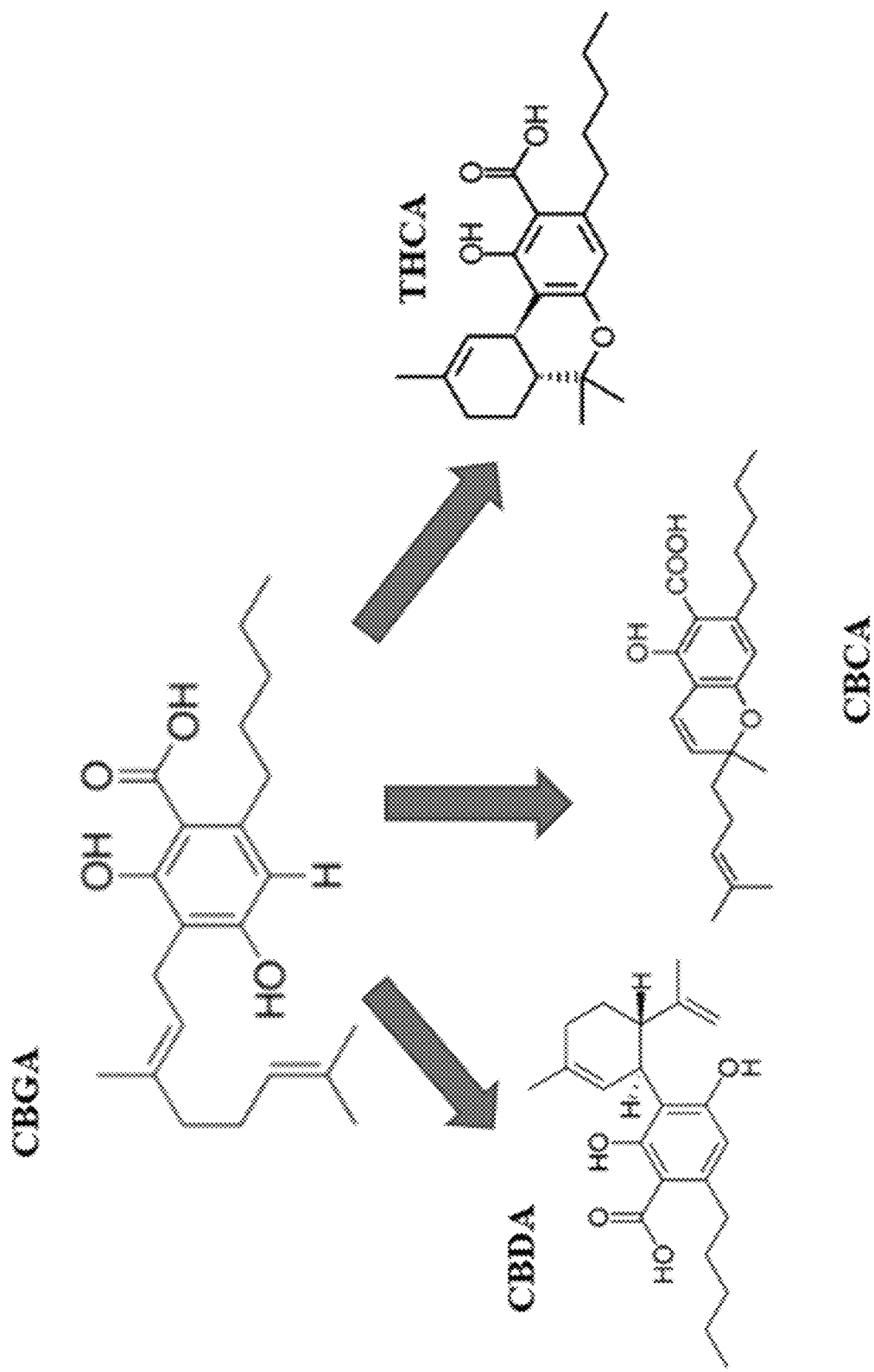
FIG. 5 shows examples of cannabinoids that can be produced from various embodiments of the invention

CBGA is a direct precursor to cannabidiolate (CBDA), with CBDA synthase catalyzing the reaction. The gene encoding CBDA synthase will be introduced into the *E. coli* strain described previously that produces CBGA. The *E. coli* strain will thus produce CBDA after growth. This will be confirmed by running the fermentation broth (diluted with acetonitrile) through a UPLC-MS/MS system as described previously and comparing the obtained signal to internal standard signals. FIG. 5 displays examples of CBGA derivatives that can be produced in accordance with the present invention, with transformation of just one additional enzyme for each derivative.

Example 4

Large-Scale Fermentation and Downstream Recovery

To produce large amounts of cannabinoids of interests, the microorganisms can be grown in large-scale fermenters rather than just shake flasks. Solvent-solvent extraction with acetonitrile will separate the cannabinoids from the fermentation broth as well as remove any cannabinoids preparative liquid chromatography system to separate and identify the desired cannabinoid from other byproducts, as well as quantify its concentration. The fraction of the preparative LC output stream containing the desired cannabinoid will be collected and lyophilized to purify the cannabinoid of interest.

Common Methods Section

Limonene Shake Flask:

Electrocompetent *E. coli* strains were transformed with pJBEI-6409 (SEQ ID NO. 11) through electroporation and recovered in 300 µL of low salt LB media for 2 hours at 37° C. in a shaking incubator set to 200 rpm. 100 µL of recovered *E. coli* were plated on ampicillin agar plates and incubated at 37° C. overnight. A colony from the ampicillin agar plate was used to start a culture in 5 mL of low salt LB media supplemented with 100 µg/mL ampicillin and left overnight at 37° C. in a shaking incubator set to 200 rpm. 500 µL of the culture was then placed in 250 mL Erlenmeyer flask with 50 mL of SM10+ media supplemented with 100 µg/mL ampicillin. This culture was placed in a 37° C. shaking incubator set to 150 rpm for approximately 5 hours until the OD was between 5 and 10. The culture was then washed with SM10− media and resuspended in 50 mL SM10− media supplemented with 100 µg/mL ampicillin and 50 µL IPTG. The culture was then left overnight at 37° C. in a shaking incubator set to 150 rpm. The OD was measured after incubating overnight and 10 mL of the culture was then mixed with 10 mL of acetonitrile to free any remaining limonene in the cells. This solution was centrifuged for 20 minutes at 10000 rpm and 4° C. The supernatant was then put into 1 mL aliquots for analysis.

Hexanoyl-CoA/FadD Mutant Shake Flask:

Electrocompetent *E. coli* strains were transformed with the FadD gene modification (SEQ ID NO. 10) (made earlier to disable fadE), by the method of electroporation, and recovered in 300 µL of low salt LB media for 2 hours at 37° C. in a shaking incubator set to 200 rpm. 100 µL of recovered *E. coli* were plated on agar plates and incubated at 37° C. overnight. A colony from the ampicillin agar plate was used to start a culture in 5 mL of low salt LB media supplemented with 100 µg/mL ampicillin and left overnight at 37° C. in a shaking incubator set to 200 rpm. 500 µL of the culture was then placed in 250 mL Erlenmeyer flask with 50 mL of SM10+ media. This culture was placed in a 37° C. shaking incubator set to 150 rpm for approximately 5 hours until the OD was between 5 and 10. The culture was then washed with SM10− media and resuspended in 50 mL SM10− media supplemented with hexanoate and without. The culture was then left overnight at 37° C. in a shaking incubator set to 150 rpm. The OD was measured after incubating overnight and 10 mL of the culture were then obtained. This solution was centrifuged for 20 minutes at 10000 rpm and 4° C. The pellet was collected and analyzed using the RapidFire mass spectroscopy machine, which essentially utilized a number of standard curves (3) calculated using known concentrations of Hexanoyl CoA in order to establish a concentration curve and the extracted pellet samples. The extraction process has not yet been identified, but generally relies on mixing with acetonitrile and lysing the cell, allowing the hexanoyl CoA to be released and collected for measurement.

Cannabigerolic Acid Shake Flask:

Electrocompetent *E. coli* strains were transformed with a variation pJBEI-6409 (SEQ ID NO. 11)(encoding the mevalonate pathway up to the creation of GPP, but not producing limonene) and pAdim (containing SEQ ID NO. 9) through electroporation and recovered in 300 µL of low salt LB media for 2 hours at 37° C. in a shaking incubator set to 200 rpm. 100 µL of recovered *E. coli* were plated on chloramphenicol and kanamycin agar plates and incubated at 37° C. overnight. A colony from the dual antibiotic agar plate was used to start a culture in 5 mL of low salt LB media supplemented with 35 µg/mL chloramphenicol and 50 µg/mL kanamycin and left overnight at 37° C. in a shaking incubator set to 200 rpm. 500 µL of the culture was then placed in 250 mL Erlenmeyer flask with 50 mL of SM10+ media, supplemented with 35 µg/mL chloramphenicol, 50 µg/mL kanamycin, and 50 µL IPTG. This culture was placed in a 37° C. shaking incubator set to 150 rpm for approximately 5 hours until the OD was between 5 and 10. The culture was then washed with SM10− media and resuspended in 50 mL SM10-media supplemented with 25 µg/mL chloramphenicol and 50 µg/mL kanamycin and 50 µL IPTG. The culture was then left overnight at 37° C. in a shaking incubator set to 150 rpm. The OD was measured after incubating overnight and 10 mL of the culture was then mixed with 10 µL of acetonitrile. This solution was centrifuged for 20 minutes at 10000 rpm and 4° C. The supernatant was then put into 1 mL aliquots for analysis.

UPLC-MS/MS Analytical Method:

Chromatography was performed using a Waters Acquity UPLC on a Restek ARC Raptor $C_{18}$ column (50 mm length with 1.8 µm particles). Column temperature was maintained at 30° C. The mobile phase was 25:75 v/v water (with 0.2% formic acid and 0.05% ammonium hydroxide) and acetonitrile with a flow rate of 1.0 mL/min and an injection volume of 2 µL. Total run time for each injection was 2 minutes.

Mass spectrometry was performed using a Xevo TQD tandem MS/MS system with an ESI source. The capillary voltage was set to 1.5 kV. The cone gas flow rate was maintained at 10 L/hr, and the desolvation gas was heated to 350° C. and maintained at 650 L/hr. Cone voltage was set to 25V for olivetolate and 15V for CBGA, with collision energies set to 15V and 25V respectively. Multiple reaction monitoring (MRM) was used for quantifications. The m/z transitions monitored were 223.25 to 179.4 and 359.35 to 341.24 for olivetolate and CBGA, respectively.

While there have been shown and described and pointed out fundamental novel features of the invention as applied to preferred embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice.

What is claimed is:

1. A method for producing at least one cannabinoid from a carbon source precursor, comprising:

genetically modifying a microorganism to express enzymes olivetol synthase, olivetolic acid cyclase, and CsPT1 for converting the carbon source precursor into at least one cannabinoid within the genetically modified microorganism wherein the microorganism is E. coli comprising a recombinantly incorporated mutated FadD gene having a nucleotide sequence of SEQ ID NO: 10 at the genomic location of a FadE gene of the microorganism to express the mutated FadD enzyme and simultaneously knock out the FadE gene of the microorganism, wherein the olivetol synthase comprises the amino acid sequence of SEQ ID NO: 2, wherein the olivetolic acid cyclase comprises the amino acid sequence of SEQ ID NO: 4, and wherein the CsPT1 comprises the amino acid sequence of SEQ ID NO: 6.

2. The method according to claim 1, wherein the carbon source precursor is glucose and the method further comprises converting the glucose to hexanoate.

3. The method according to claim 2, wherein the at least one cannabinoid comprises cannabigerolic acid.

4. The method according to claim 1, wherein genetically modifying the bacterial strain comprises transforming the bacterial strain with a plasmid having a nucleotide sequence comprising the nucleotide sequence of SEQ ID NO: 9.

5. The method according to claim 4, wherein the plasmid comprises a nucleotide sequence for a Glutathione-S-Transferase (GST) solubility tag and a thrombin cleavage site having the amino acid sequence of SEQ ID NO: 8 in the same open reading frame as CsPT1.

6. The method according to claim 1, further comprising extracting the at least one cannabinoid produced by the genetically modified microorganism from a fermentation broth comprising the genetically modified microorganism.

7. The method according to claim 1, wherein genetically modifying the bacterial strain comprises the addition of recombineered metabolic protein degradation valves for one or more of a pgi gene, a zwf gene and a gltA gene by adding a C-terminal DAS+4 tag having the nucleotide sequence SEQ ID NO: 12 to the respective one or more of the pgi gene, the zwf gene and the gltA gene.

8. A method for producing at least one cannabinoid from a carbon source precursor, comprising:
  genetically modifying a microorganism to express enzymes olivetol synthase, olivetolic acid cyclase, and CsPT1 and converting the carbon source precursor into at least one cannabinoid within the genetically modified microorganism, wherein the microorganism is *S. cerevisiae* and has been transformed with a plasmid to express a polypeptide encoding olivetol synthase having the amino acid sequence of SEQ ID NO: 2, a polypeptide encoding olivetolic acid cyclase having the amino acid sequence of SEQ ID NO: 4, a polypeptide encoding CsPT1 having the amino acid sequence of SEQ ID NO: 6, and further comprising a Glutathione-S-Transferase (GST) solubility tag with a thrombin cleavage site having the amino acid sequence of SEQ ID NO: 8 in the same open reading frame as CsPT1.

9. The method according to claim 8, wherein transforming the *S. cerevisiae* further comprises transforming the *S. cerevisiae* with the plasmid further having a nucleotide sequence comprising the nucleotide sequence of SEQ ID NO: 9.

10. The method according to claim 8, wherein genetically modifying the *S. cerevisiae* comprises the addition of recombineered metabolic protein degradation valves for one or more of a pgi gene, a zwf gene and a gltA gene by adding a C-terminal DAS+4 tag having the nucleotide sequence SEQ ID NO: 12 to the respective one or more of the pgi gene, the zwf gene and the gltA gene.

* * * * *

SEQUENCE LISTING

```
<160> NUMBER OF SEQ ID NOS: 12

<210> SEQ ID NO 1
<211> LENGTH: 1158
<212> TYPE: DNA
<213> ORGANISM: Artificial Sequence
<220> FEATURE:
<223> OTHER INFORMATION: Codon optimized for E. coli

<400> SEQUENCE: 1
atgaaccatt tgcgtgcaga aggccccgca tcagtcctgg ctattggaac agcaaacccg      60
gaaaacatct tactgcaaga cgaatttccg gactactact tccgtgtaac gaaatccgaa     120
cacatgacgc aactgaaaga gaaatttcgc aaaatctgtg ataagtcaat gatccgtaaa     180
cgtaattgtt tcttgaatga ggagcattta aaacaaaatc cgcgcttagt agagcatgag     240
atgcaaactc tggacgcccg tcaagacatg ttagttgtcg aagtccccaa attgggtaaa     300
gatgcgtgtg ctaaggctat taaggagtgg ggacaaccaa agagtaagat tactcattta     360
atttttacta gcgcgtctac aaccgatatg cccggtgccg attatcactg cgcaaaattg     420
ctgggtctta gtccaagtgt aaaacgtgta atgatgtatc agctgggctg ttacggggc      480 gggacagtgc tgcgcattgc aaaggatatc gcagagaaca ataaaggagc ccgtgtttta     540
gctgtatgct gcgatattat ggcgtgctta ttccgtgggc cgtctgaatc ggacttagag     600
ctgttagtag ggcaggctat ttttggcgat ggagctgccg ccgtgattgt cggagcggag     660
ccggatgaat ctgtaggcga gcgccccatc tttgagttgg tatcaactgg ccagaccatt     720
ctgccaaaca gtgagggcac gattggcgga cacatccgtg aagcaggact tattttcgat     780
ctgcacaagg atgtgcccat gttaatttca aacaacattg agaagtgctt aatcgaggct     840
ttcacgccga ttggtatctc ggattggaat tccattttct ggatcaccca tcccggaggc     900
aaagctattt tggacaaagt ggaggagaaa ttacacctga aaagtgacaa gtttgtagat     960
agtcgtcatg ttttatccga gcacggcaat atgtcatcat ctactgtact gtttgtcatg    1020
gacgagttgc gcaaacgctc cttagaagaa ggtaagagca cgactggcga cggctttgag    1080
tggggagtcc tgtttggctt tggtcctgga cttacggtcg aacgcgtggt tgtgcgctca    1140
gtgccgatta aatattaa                                                  1158

<210> SEQ ID NO 2
<211> LENGTH: 385
<212> TYPE: PRT
<213> ORGANISM: Artificial Sequence
<220> FEATURE:
<223> OTHER INFORMATION: Polypeptide encoded by SEQ ID NO. 1

<400> SEQUENCE: 2

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
```

20                  25                  30
    Tyr Phe Arg Val Thr Lys Ser Glu His Met Thr Gln Leu Lys Glu Lys
                35                  40                  45

Phe Arg Lys Ile Cys Asp Lys Ser Met Ile Arg Lys Arg Asn Cys Phe
        50                  55                  60

Leu Asn Glu Glu His Leu Lys Gln Asn Pro Arg Leu Val Glu His Glu
    65                  70                  75                  80

Met Gln Thr Leu Asp Ala Arg Gln Asp Met Leu Val Val Glu Val Pro
                    85                  90                  95

Lys Leu Gly Lys Asp Ala Cys Ala Lys Ala Ile Lys Glu Trp Gly Gln
                100                 105                 110

Pro Lys Ser Lys Ile Thr His Leu Ile Phe Thr Ser Ala Ser Thr Thr
                115                 120                 125

Asp Met Pro Gly Ala Asp Tyr His Cys Ala Lys Leu Leu Gly Leu Ser
                130                 135                 140

Pro Ser Val Lys Arg Val Met Met Tyr Gln Leu Gly Cys Tyr Gly Gly
    145                 150                 155                 160

Gly Thr Val Leu Arg Ile Ala Lys Asp Ile Ala Glu Asn Asn Lys Gly
                    165                 170                 175

Ala Arg Val Leu Ala Val Cys Cys Asp Ile Met Ala Cys Leu Phe Arg
                180                 185                 190

Gly Pro Ser Glu Ser Asp Leu Glu Leu Leu Val Gly Gln Ala Ile Phe
                195                 200                 205

Gly Asp Gly Ala Ala Ala Val Ile Val Gly Ala Glu Pro Asp Glu Ser
                210                 215                 220

Val Gly Glu Arg Pro Ile Phe Glu Leu Val Ser Thr Gly Gln Thr Ile
    225                 230                 235                 240

Leu Pro Asn Ser Glu Gly Thr Ile Gly Gly His Ile Arg Glu Ala Gly
                    245                 250                 255

Leu Ile Phe Asp Leu His Lys Asp Val Pro Met Leu Ile Ser Asn Asn
                260                 265                 270

Ile Glu Lys Cys Leu Ile Glu Ala Phe Thr Pro Ile Gly Ile Ser Asp
                275                 280                 285

Trp Asn Ser Ile Phe Trp Ile Thr His Pro Gly Gly Lys Ala Ile Leu
                290                 295                 300

Asp Lys Val Glu Glu Lys Leu His Leu Lys Ser Asp Lys Phe Val Asp
    305                 310                 315                 320

Ser Arg His Val Leu Ser Glu His Gly Asn Met Ser Ser Ser Thr Val
                    325                 330                 335

Leu Phe Val Met Asp Glu Leu Arg Lys Arg Ser Leu Glu Glu Gly Lys
                340                 345                 350

Ser Thr Thr Gly Asp Gly Phe Glu Trp Gly Val Leu Phe Gly Phe Gly
                355                 360                 365

Pro Gly Leu Thr Val Glu Arg Val Val Val Arg Ser Val Pro Ile Lys
                370                 375                 380

Tyr
    385

<210> SEQ ID NO 3
<211> LENGTH: 306
<212> TYPE: DNA
<213> ORGANISM: Artificial Sequence
<220> FEATURE:
<223> OTHER INFORMATION: Codon optimized for E. coli

<400> SEQUENCE: 3

```
atggccgtca agcaccttat tgtgctgaaa ttcaaggacg aaatcaccga ggcgcaaaaa    60
gaagagttct ttaagactta cgtgaacctt gtgaatatca ttcctgcaat gaaggatgtg   120
tattggggta agatgtcac tcaaaaaaac aaggaagagg ggtataccca catcgtagaa   180
gtgaccttcg aatcggtaga gactatccag gactatatta tccacccccgc gcacgtcggg   240
tttggcgacg tgtaccgttc attctgggaa aagctgttga tcttcgatta cccccccgc   300
aagtaa                                                              306
```

<210> SEQ ID NO 4
<211> LENGTH: 101
<212> TYPE: PRT
<213> ORGANISM: Artificial Sequence
<220> FEATURE:
<223> OTHER INFORMATION: Polypeptide encoded by SEQ ID NO. 3

<400> SEQUENCE: 4

```
Met Ala Val Lys His Leu Ile Val Leu Lys Phe Lys Asp Glu Ile Thr
1               5                   10                  15
Glu Ala Gln Lys Glu Glu Phe Phe Lys Thr Tyr Val Asn Leu Val Asn
            20                  25                  30
Ile Ile Pro Ala Met Lys Asp Val Tyr Trp Gly Lys Asp Val Thr Gln
        35                  40                  45
Lys Asn Lys Glu Glu Gly Tyr Thr His Ile Val Glu Val Thr Phe Glu
    50                  55                  60
Ser Val Glu Thr Ile Gln Asp Tyr Ile Ile His Pro Ala His Val Gly
65                  70                  75                  80
Phe Gly Asp Val Tyr Arg Ser Phe Trp Glu Lys Leu Leu Ile Phe Asp
                85                  90                  95
Tyr Thr Pro Arg Lys
            100
```

<210> SEQ ID NO 5
<211> LENGTH: 969
<212> TYPE: DNA
<213> ORGANISM: Artificial Sequence
<220> FEATURE:
<223> OTHER INFORMATION: Codon optimized for E. coli

<400> SEQUENCE: 5

```
ccaggagcgg caactaccaa tcaaaccgag cctccagagt ctgataatca ttcagttgca    60
actaaaattc tgaattttgg taaggcgtgc tggaaactgc aacgtcctta cacaatcatt   120
gcctttacct catgtgcctg cggcttattc ggaaaggaac ttttacacaa cacaaactta   180
atctcttggt cccttatgtt caaagcgttc ttttttcttg ttgcgatcct gtgtattgcg   240
agctttacta cgactattaa tcagatttac gatcttcaca ttgaccgtat caacaaacca   300
gaccttcccc ttgcctcagg ggaaatctct gtcaacactg cttggattat gtccattatc   360
gtcgcccttt ttggcttaat tatcacaatc aagatgaaag gtggtccgtt atacattttt   420
ggctactgct tcggcatttt tggggggatt gtttactccg tcccgccatt tcgctggaaa   480
cagaacccta gcacagcttt cctgttaaac ttcttagctc atatcatcac aaactttaca   540
ttttattacg caagccgcgc tgctttaggg ctgcccttg aactgcgccc ttcattcacc   600
ttcctgttag cattcatgaa gagtatgggt tctgcactgg cacttatcaa agacgctagt   660
gatgtagagg gagatacaaa gttcggcatc agtacgttgg cctcgaaata cggcagccgt   720
```

```
aacttaacac ttttttgctc cgggattgtc ttgttgtcat atgtggctgc gatcttggca    780
ggcattatct ggccccaggc gttcaacagt aatgtgatgc ttctgtctca cgctattttg    840 gcttttggt tgatccttca aacgcgcgat tttgcgttaa cgaattatga ccctgaagct     900
ggtcgccgtt tctatgaatt tatgtggaaa ctttattatg cggagtattt ggtgtacgta    960
tttatctaa                                                           969
```

<210> SEQ ID NO 6
<211> LENGTH: 322
<212> TYPE: PRT
<213> ORGANISM: Artificial Sequence
<220> FEATURE:
<223> OTHER INFORMATION: Polypeptide encoded by SEQ ID NO. 5

<400> SEQUENCE: 6

```
Pro Gly Ala Ala Thr Thr Asn Gln Thr Glu Pro Pro Glu Ser Asp Asn
 1               5                  10                  15

His Ser Val Ala Thr Lys Ile Leu Asn Phe Gly Lys Ala Cys Trp Lys
            20                  25                  30

Leu Gln Arg Pro Tyr Thr Ile Ile Ala Phe Thr Ser Cys Ala Cys Gly
        35                  40                  45

Leu Phe Gly Lys Glu Leu Leu His Asn Thr Asn Leu Ile Ser Trp Ser
    50                  55                  60

Leu Met Phe Lys Ala Phe Phe Leu Val Ala Ile Leu Cys Ile Ala
65                  70                  75                  80

Ser Phe Thr Thr Thr Ile Asn Gln Ile Tyr Asp Leu His Ile Asp Arg
                85                  90                  95

Ile Asn Lys Pro Asp Leu Pro Leu Ala Ser Gly Glu Ile Ser Val Asn
            100                 105                 110

Thr Ala Trp Ile Met Ser Ile Val Ala Leu Phe Gly Leu Ile Ile
        115                 120                 125

Thr Ile Lys Met Lys Gly Gly Pro Leu Tyr Ile Phe Gly Tyr Cys Phe
    130                 135                 140

Gly Ile Phe Gly Gly Ile Val Tyr Ser Val Pro Pro Phe Arg Trp Lys
145                 150                 155                 160

Gln Asn Pro Ser Thr Ala Phe Leu Leu Asn Phe Leu Ala His Ile Ile
                165                 170                 175

Thr Asn Phe Thr Phe Tyr Tyr Ala Ser Arg Ala Ala Leu Gly Leu Pro
            180                 185                 190

Phe Glu Leu Arg Pro Ser Phe Thr Phe Leu Leu Ala Phe Met Lys Ser
        195                 200                 205

Met Gly Ser Ala Leu Ala Leu Ile Lys Asp Ala Ser Asp Val Glu Gly
    210                 215                 220

Asp Thr Lys Phe Gly Ile Ser Thr Leu Ala Ser Lys Tyr Gly Ser Arg
225                 230                 235                 240

Asn Leu Thr Leu Phe Cys Ser Gly Ile Val Leu Leu Ser Tyr Val Ala
                245                 250                 255

Ala Ile Leu Ala Gly Ile Ile Trp Pro Gln Ala Phe Asn Ser Asn Val
            260                 265                 270

Met Leu Leu Ser His Ala Ile Leu Ala Phe Trp Leu Ile Leu Gln Thr
        275                 280                 285

Arg Asp Phe Ala Leu Thr Asn Tyr Asp Pro Glu Ala Gly Arg Arg Phe
    290                 295                 300

Tyr Glu Phe Met Trp Lys Leu Tyr Ala Glu Tyr Leu Val Tyr Val
305                 310                 315                 320
```

Phe Ile

<210> SEQ ID NO 7
<211> LENGTH: 678
<212> TYPE: DNA
<213> ORGANISM: Artificial Sequence
<220> FEATURE:
<223> OTHER INFORMATION: Synthetic polynucleotide

<400> SEQUENCE: 7

```
atgtcccctta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600
tggcctttgc agggctggca agccacgttt ggtggtggcg accatcctcc aaaatcggat     660
ctggttccgc gtggatcc                                                   678
```

<210> SEQ ID NO 8
<211> LENGTH: 226
<212> TYPE: PRT
<213> ORGANISM: Artificial Sequence
<220> FEATURE:
<223> OTHER INFORMATION: Polypeptide encoded by SEQ ID NO. 7

<400> SEQUENCE: 8

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
        210                 215                 220

Gly Ser
225

<210> SEQ ID NO 9
<211> LENGTH: 5247
<212> TYPE: DNA
<213> ORGANISM: Artificial Sequence
<220> FEATURE:
<223> OTHER INFORMATION: Synthetic plasmid polynucleotide

<400> SEQUENCE: 9
```

| | | | | | |
|---|---|---|---|---|---|
| cattgcacaa | tacgactcac | tatagggaga | ccacaacggt | ttcccactag | aaataatttt | 60 |
| gtttaacttt | aagaaggaga | tatacatatg | aaccatttgc | gtgcagaagg | ccccgcatca | 120 |
| gtcctggcta | ttggaacagc | aaacccggaa | acatcttac | tgcaagacga | atttccggac | 180 |
| tactacttcc | gtgtaacgaa | atccgaacac | atgacgcaac | tgaaagagaa | atttcgcaaa | 240 |
| atctgtgata | agtcaatgat | ccgtaaacgt | aattgtttct | tgaatgagga | gcatttaaaa | 300 |
| caaaatccgc | gcttagtaga | gcatgagatg | caaactctgg | acgcccgtca | agacatgtta | 360 |
| gttgtcgaag | tccccaaatt | gggtaaagat | gcgtgtgcta | aggctattaa | ggagtgggga | 420 |
| caaccaaaga | gtaagattac | tcatttaatt | tttactagcg | cgtctacaac | cgatatgccc | 480 |
| ggtgccgatt | atcactgcgc | aaaattgctg | ggtcttagtc | caagtgtaaa | acgtgtaatg | 540 |
| atgtatcagc | tgggctgtta | cgggggcggg | acagtgctgc | gcattgcaaa | ggatatcgca | 600 |
| gagaacaata | aaggagcccg | tgttttagct | gtatgctgcg | atattatggc | gtgcttattc | 660 |
| cgtgggccgt | ctgaatcgga | cttagagctg | ttagtagggc | aggctatttt | tggcgatgga | 720 |
| gctgccgccg | tgattgtcgg | agcggagccg | gatgaatctg | taggcgagcg | ccccatcttt | 780 |
| gagttggtat | caactggcca | gaccattctg | ccaaacagtg | agggcacgat | tggcggacac | 840 |
| atccgtgaag | caggacttat | tttcgatctg | cacaaggatg | tgcccatgtt | aatttcaaac | 900 |
| aacattgaga | agtgcttaat | cgaggctttc | acgccgattg | gtatctcgga | ttggaattcc | 960 |
| attttctgga | tcacccatcc | cggaggcaaa | gctattttgg | acaaagtgga | ggagaaatta | 1020 |
| cacctgaaaa | gtgacaagtt | tgtagatagt | cgtcatgttt | tatccgagca | cggcaatatg | 1080 |
| tcatcatcta | ctgtactgtt | tgtcatggac | gagttgcgca | aacgctcctt | agaagaaggt | 1140 |
| aagagcacga | ctggcgacgg | ctttgagtgg | ggagtcctgt | ttggctttgg | tcctggactt | 1200 |
| acggtcgaac | gcgtggttgt | gcgctcagtg | ccgattaaat | attaattcac | acaggaaaca | 1260 |
| gtattcatgt | ccctatact | aggttattgg | aaaattaagg | gccttgtgca | acccactcga | 1320 |
| cttcttttgg | aatatcttga | agaaaaatat | gaagagcatt | tgtatgagcg | cgatgaaggt | 1380 |
| gataaatggc | gaaacaaaaa | gtttgaattg | ggtttggagt | ttcccaatct | tccttattat | 1440 |
| attgatggta | atgttaaatt | aacacagtct | atggccatca | tacgttatat | agctgacaag | 1500 |
| cacaacatgt | tgggtggttg | tccaaaagag | cgtgcagaga | tttcaatgct | tgaaggagcg | 1560 |
| gttttggata | ttagatacgg | tgtttcgaga | attgcatata | gtaaagactt | tgaaactctc | 1620 |
| aaagttgatt | ttcttagcaa | gctacctgaa | atgctgaaaa | tgttcgaaga | tcgtttatgt | 1680 |

| | |
|---|---|
| cataaaacat atttaaatgg tgatcatgta acccatcctg acttcatgtt gtatgacgct | 1740 |
| cttgatgttg ttttatacat ggacccaatg tgcctggatg cgttcccaaa attagtttgt | 1800 |
| tttaaaaaac gtattgaagc tatcccacaa attgataagt acttgaaatc cagcaagtat | 1860 |
| atagcatggc ctttgcaggg ctggcaagcc acgtttggtg gtggcgacca tcctccaaaa | 1920 |
| tcggatctgg ttccgcgtgg atccccagga gcggcaacta ccaatcaaac cgagcctcca | 1980 |
| gagtctgata atcattcagt tgcaactaaa attctgaatt ttggtaaggc gtgctggaaa | 2040 |
| ctgcaacgtc cttacacaat cattgccttt acctcatgtg cctgcggctt attcggaaag | 2100 |
| gaacttttac acaacacaaa cttaatctct tggtcccctta tgttcaaagc gttctttttt | 2160 |
| cttgttgcga tcctgtgtat tgcgagcttt actacgacta ttaatcagat ttacgatctt | 2220 |
| cacattgacc gtatcaacaa accagaccct cccctttgcct caggggaaat ctctgtcaac | 2280 |
| actgcttgga ttatgtccat tatcgtcgcc cttttttggct taattatcac aatcaagatg | 2340 |
| aaaggtggtc cgttatacat ttttggctac tgcttcggca tttttggggg gattgtttac | 2400 |
| tccgtcccgc catttcgctg gaaacagaac cctagcacag ctttcctgtt aaacttctta | 2460 |
| gctcatatca tcacaaactt tacattttat tacgcaagcc gcgctgcttt agggctgccc | 2520 |
| tttgaactgc gcccttcatt caccttcctg ttagcattca tgaagagtat gggttctgca | 2580 |
| ctggcactta tcaaagacgc tagtgatgta gagggagata caaagttcgg catcagtacg | 2640 |
| ttggcctcga aatacggcag ccgtaactta acacttttttt gctccgggat tgtcttgttg | 2700 |
| tcatatgtgg ctgcgatctt ggcaggcatt atctggcccc aggcgttcaa cagtaatgtg | 2760 |
| atgcttctgt ctcacgctat tttggctttt tggttgatcc ttcaaacgcg cgattttgcg | 2820 |
| ttaacgaatt atgaccctga agctggtcgc cgtttctatg aatttatgtg gaaactttat | 2880 |
| tatgcggagt atttggtgta cgtatttatc taacaggagc taaggaagct aaaatggccg | 2940 |
| tcaagcacct tattgtgctg aaattcaagg acgaaatcac cgaggcgcaa aaagaagagt | 3000 |
| tctttaagac ttacgtgaac cttgtgaata tcattcctgc aatgaaggat gtgtattggg | 3060 |
| gtaaagatgt cactcaaaaa aacaaggaag aggggtatac ccacatcgta gaagtgacct | 3120 |
| tcgaatcggt agagactatc caggactata ttatccaccc cgcgcacgtc gggttttggcg | 3180 |
| acgtgtaccg ttcattctgg gaaaagctgt tgatcttcga ttacaccccc cgcaagtaat | 3240 |
| aatgactcga gtctggtaaa actagcattc gacctagcat aaccccgcgg ggcctcttcg | 3300 |
| ggggtctcgc ggggtttttt gctgaaagaa gcttcaaata aaacgaaagg ctcagtcgaa | 3360 |
| agactgggcc tttcgtttta tctgttgttt gtcgctgcgg ccgggtcagg tatgatttaa | 3420 |
| atggtcagta acgggtcttg aggggttttt tgcaatgggg acgaattctc tagatatcgc | 3480 |
| tcaatactga ccatttaaat catacctgac ctccatagca gaaagtcaaa gcctccgac | 3540 |
| cggaggcttt tgacttgatc ggcacgtaag aggttccaac tttcaccata atgaaataag | 3600 |
| atcactaccg ggcgtatttt ttgagttatc gagattttca ggagctaagg aagctaaaat | 3660 |
| gagccatatt caacgggaaa cgtcttgctc gaggccgcga ttaaattcca acatggatgc | 3720 |
| tgatttatat gggtataaat gggctcgcga taatgtcggg caatcaggtg cgacaatcta | 3780 |
| tcgattgtat gggaagcccg atgcgccaga gttgttctg aaacatggca aaggtagcgt | 3840 |
| tgccaatgat gttacagatg agatggtcag gctaaactgg ctgacggaat ttatgcctct | 3900 |
| tccgaccatc aagcatttta tccgtactcc tgatgatgca tggttactca ccactgcgat | 3960 |
| cccagggaaa acagcattcc aggtattaga agaatatcct gattcaggtg aaaatattgt | 4020 |
| tgatgcgctg gcagtgttcc tgcgccggtt gcattcgatt cctgtttgta attgtcctttt | 4080 |

-continued

```
taacggcgat cgcgtatttc gtctcgctca ggcgcaatca cgaatgaata acggtttggt    4140
tggtgcgagt gattttgatg acgagcgtaa tggctggcct gttgaacaag tctggaaaga    4200
aatgcataag cttttgccat tctcaccgga ttcagtcgtc actcatggtg atttctcact    4260
tgataacctt attttgacg aggggaaatt aataggttgt attgatgttg acgagtcgg     4320 aatcgcagac cgataccagg atcttgccat cctatggaac tgcctcggtg agttttctcc    4380
ttcattacag aaacggcttt ttcaaaaata tggtattgat aatcctgata tgaataaatt    4440
gcagtttcac ttgatgctcg atgagttttt ctaatgaggg cccaaatgta atcacctggc    4500
tcaccttcgg gtgggccttt ctgcgttgct ggcgttttc cataggctcc gccccctga    4560 cgagcatcac aaaaatcgat gctcaagtca gaggtggcga acccgacag gactataaag    4620 ataccaggcg tttccccctg gaagctccct cgtgcgctct cctgttccga ccctgccgct    4680
taccggatac ctgtccgcct ttctcccttc gggaagcgtg gcgctttctc atagctcacg    4740
ctgtaggtat ctcagttcgg tgtaggtcgt tcgctccaag ctgggctgtg tgcacgaacc    4800
ccccgttcag cccgaccgct gcgccttatc cggtaactat cgtcttgagt ccaacccggt    4860
aagacacgac ttatcgccac tggcagcagc cactggtaac aggattagca gagcgaggta    4920
tgtaggcggt gctacagagt tcttgaagtg gtggcctaac tacggctaca ctagaagaac    4980
agtatttggt atctgcgctc tgctgaagcc agttacctcg gaaaaagagt tggtagctct    5040
tgatccggca aacaaaccac cgctggtagc ggtggttttt ttgtttgcaa gcagcagatt    5100
acgcgcagaa aaaaggatc tcaagaagat cctttgattt tctaccgaag aaaggcccac    5160
ccgtgaaggt gagccagtga gttgattgca gtccagttac gctggagtct gaggctcgtc    5220
ctgaatgata tcaagcttga attcgtt                                        5247
```

<210> SEQ ID NO 10
<211> LENGTH: 3000
<212> TYPE: DNA
<213> ORGANISM: Artificial Sequence
<220> FEATURE:
<223> OTHER INFORMATION: Synthetic polynucleotide

<400> SEQUENCE: 10

```
cttcagcata aatgtaatag acaaaatgca gtgtaccgga taccgccaaa agcgagaagt      60
acgggcaggt gctatgacca ggactttttg cacagctaac accacgtcgt ccctatctgc     120
tgccctaggt ctatgagtgg ttgctggata actttacggg catgcataag gctcgtataa    180
tatattcagg gagaccacaa cggtttccct ctacaaataa ttttgtttaa ctttcaggag    240
ctaaggaagc taaatgaag aaagtctggt taaatcgtta ccccgccgat gtgcccacag     300
aaatcaaccc agaccgttat caatcgttgg tagacatgtt tgagcaatcc gtagcacgct    360
acgctgacca gccagcctc gtaaatatgg gtgaggtaat gacctttcgt aaattagaag    420
aacgttcccg tgccttcgct gcatatctgc aacagggact tgggttaaaa aaaggcgatc    480
gcgtggcgtt gatgatgccc aacctgttgc aatacctgt tgcgcttttc ggcatccttc    540
gcgctgggat gatcgttgta aatgtcaatc cgttgtacac cccgcgtgag ctggagcacc    600
aacttaatga cagcggagca agcgcaattg ttatcgtttc aaactttgcc cacacactgg    660
aaaaggttgt ggataaaaca gccgttcagc atgtcatcct tacacgcatg ggcgatcagt    720
tgtccacggc caaggtacg gtcgtgaatt tcgttgttaa atacattaag cgcttagtac     780
ccaaatacca tcttccagat gcaatcagtt tccgcagcgc attacataac gggtaccgta    840
```

```
tgcagtatgt taagcccgaa ctggtgccag aggaccttgc attttttacag tacactgggg    900
ggacaaccgg agtggcaaaa ggggcgatgt tgactcaccg caatatgctt gccaatctgg    960
aacaggttaa tgcaacctat ggtccgctgt tacaccctgg caaagaatta gtagtgacag   1020
cattaccgct ttatcatatt ttcgctctta ctatcaattg cttattgttt attgagctgg   1080
gagggcaaaa ccttctgatt actaacccac gcgatattcc gggacttgtg aaggagctgg   1140
ctaagtaccc gtttacagca attactggtg tcaacacact gtttaatgca ctgctgaata   1200
acaaggaatt tcaacagtta gacttcagta gtcttcattt gtcggcgggt ggaggaatgc   1260
ctgtgcaaca agtggtggcg gaacgttggg tgaaattaac aggccagtat ttgttagagg   1320
gatacggcct gacagagtgt gcgcccttag tcagcgttaa cccatatgac attgattacc   1380
attcgggtag cattggttta ccagtcccgt ctactgaagc aaaattggta gacgatgatg   1440
acaatgaagt tccgccggga cagccgggcg aactttgtgt aaagggtcct caggtcatgt   1500
tagggtactg gcaacgtccc gacgctacag atgagattat caaaaacggg tggcttcata   1560
caggcgatat cgctgtaatg gatgaggagg gtttcttacg tatcgcagat cgtaagaaag   1620
atatgatttt agtaagtgga ttcaatgtgt acccgaacga aatcgaagat gtagtaatgc   1680
aacatcccgg tgtccaggag gttgcggccg tgggtgttcc atccggctcc agcggggaag   1740
cggtcaagat ctttgtggtc aagaaagatc cgtcattgac agaggaatct cttgtaactt   1800
tttgccgccg ccaactgaca ggatacaaag ttcctaaatt ggttgaattc cgcgatgaac   1860
ttccaaaatc caacgtcgga aagatccttc gccgtgaatt acgcgatgaa gcccgtggca   1920
aagtagataa taaggcttga tgatcggcac gtaagaggtt ccaactttca ccataatgaa   1980
ataagatcac taccgggcgt atttttttgag ttatcgagat tttcaggagc taaggaagct   2040
aaaatgagta ttcaacattt ccgtgtcgcc cttattccct tttttgcggc attttgcctt   2100
cctgtttttg ctcacccaga aacgctggtg aaagtaaaag atgctgaaga tcagttgggt   2160
gcacgagtgg gttacatcga actggatctc aacagcggta agatccttga gtttacgc    2220
cccgaagaac gttttccaat gatgagcact tttaaagttc tgctatgtgg cgcggtatta   2280
tcccgtattg acgccgggca agagcaactc ggtcgccgca tacactattc tcagaatgac   2340
ttggttgagt actcaccagt cacagaaaag catctcacgg atggcatgac agtaagagaa   2400
ttatgcagtg ctgccataac catgagtgat aacactgcgg ccaacttact tctggcaacg   2460
atcggaggac cgaaggagct aaccgctttt ttgcacaaca tgggggatca tgtaactcgc   2520
cttgatcgtt gggaaccgga gctgaatgaa gccataccaa acgacgagcg tgacaccacg   2580
atgcctgtag caatggcaac aacgttgcgc aaactattaa ctggcgaact acttactcta   2640
gcttcccggc aacaattaat agactggatg gaggcggata agttgcagg atcacttctg   2700
cgctcggccc ttccggctgg ctggtttatt gctgataaat ctggagccgg tgagcgtggg   2760
tctcgcggta tcattgcagc actggggcca gatggtaagc cctcccgcat cgtagttatc   2820
tacacgacgg ggagtcaggc aactatggat gaacgaaata gacagatcgc tgagataggt   2880
gcctcactga ttaagcattg gtaaggagcc gaaaggctcc gttctcttat ccgctaatta   2940
tttaaaatta aagccatccg gatggttttc caggctgccg gtcaacgccg cgaacaacac   3000
```

<210> SEQ ID NO 11
<211> LENGTH: 13303
<212> TYPE: DNA
<213> ORGANISM: Artificial Sequence
<220> FEATURE:
<223> OTHER INFORMATION: Synthetic polynucleotide

<400> SEQUENCE: 11

```
gacgtcggtg cctaatgagt gagctaactt acattaattg cgttgcgctc actgcccgct      60
ttccagtcgg gaaacctgtc gtgccagctg cattaatgaa tcggccaacg cgcggggaga     120
ggcggtttgc gtattgggcg ccagggtggt ttttcttttc accagtgaga cgggcaacag     180
ctgattgccc ttcaccgcct ggccctgaga gagttgcagc aagcggtcca cgctggtttg     240
ccccagcagg cgaaaatcct gtttgatggt ggttaacggc gggatataac atgagctgtc     300
ttcggtatcg tcgtatccca ctaccgagat gtccgcacca acgcgcagcc cggactcggt     360
aatgcgcgc attgcgccca cgccatctg atcgttggca accagcatcg cagtgggaac      420
gatgccctca ttcagcattt gcatggtttg ttgaaaaccg acatggcac tccagtcgcc      480
ttcccgttcc gctatcggct gaatttgatt gcgagtgaga tatttatgcc agccagccag    540
acgcagacgc gccgagacag aacttaatgg gcccgctaac agcgcgattt gctggtgacc     600
caatgcgacc agatgctcca cgcccagtcg cgtaccgtct tcatgggaga aataatact     660
gttgatgggt gtctggtcag agacatcaag aaataacgcc ggaacattag tgcaggcagc     720
ttccacagca atggcatcct ggtcatccag cggatagtta atgatcagcc cactgacgcg     780
ttgcgcgaga agattgtgca ccgccgcttt acaggcttcg acgccgcttc gttctaccat    840
cgacaccacc acgctggcac ccagttgatc ggcgcgagat ttaatcgccg cgacaatttg    900
cgacggcgcg tgcagggcca gactggaggt ggcaacgcca atcagcaacg actgtttgcc    960
cgccagttgt tgtgccacgc ggttgggaat gtaattcagc tccgccatcg ccgcttccac   1020
ttttccgc gttttcgcag aaacgtggct ggcctggttc accacgcggg aaacggtctg    1080
ataagagaca ccggcatact ctgcgacatc gtataacgtt actggttca cattcaccac    1140
cctgaattga ctctcttccg ggcgctatca tgccataccg cgaaaggttt tgcgccattc   1200
gatggtgtcc gggatctcga cgctctccct tatgcgactc ctgcattagg aagcagccca    1260
gtagtaggtt gaggccgttg agcaccgccg ccgcaaggaa tggtgcatgc aaggagatgg    1320
cgcccaacag tccccccggcc acggggcctg ccaccatacc cacgccgaaa caagcgctca   1380
tgagcccgaa gtgcgagcc cgatcttccc catcggtgat gtcggcgata taggcgccag     1440
caaccgcacc tgtggcgccg gtgatgccgg ccacgatgcg tccggcgtag aggatcgaga    1500
tcgtttaggc accccaggct ttacacttta tgcttccggc tcgtataatg tgtggaattg    1560
tgagcggata caatttcag aattcaaaag atcttaggag gaatataaaa tgaaaattg     1620
tgtcatcgtc agtgcggtac gtactgctat cggtagtttt aacggttcac tcgcttccac   1680
cagcgccatc gacctggggg cgacagtaat taaagccgcc attgaacgtg caaaaatcga   1740
ttcacaacac gttgatgaag tgattatggg taacgtgtta caagccgggc tggggcaaaa   1800
tccggcgcgt caggcactgt taaaaagcgg gctggcagaa acgtgtgcg gattcacggt     1860
caataaagta tgtggttcgg gtcttaaaag tgtggcgctt ccgcccagg ccattcaggc    1920
aggtcaggcg cagagcattg tggcgggggg tatggaaaat atgagtttag ccccctactt    1980
actcgatgca aaagcacgct ctggttatcg tcttggagac ggacaggttt atgacgtaat    2040
cctgcgcgat ggcctgatgt gcgccaccca tggttatcat atggggatta ccgccgaaaa    2100
cgtggctaaa gagtacggaa ttacccgtga aatgcaggat gaactggcgc tacattcaca    2160
gcgtaaagcg gcagccgcaa ttgagtccgg tgcttttaca gccgaaatcg tcccggtaaa    2220
tgttgtcact cgaaagaaaa ccttcgtctt cagtcaagac gagttccga aagcgaactc     2280
```

```
aacggctgaa gcgttaggtg cattgcgccc ggccttcgat aaagcaggaa cagtcaccgc    2340
tgggaacgcg tctggtatta acgacggtgc tgccgctctg gtgattatgg aagaatctgc    2400
ggcgctggca gcaggcctta ccccctggc tcgcattaaa agttatgcca gcggtggcgt    2460 gcccccgca ttgatgggta tggggccagt acctgccacg caaaaagcgt tacaactggc     2520
ggggctgcaa ctgcggata ttgatctcat tgaggctaat gaagcatttg ctgcacagtt     2580
ccttgccgtt gggaaaaacc tgggctttga ttctgagaaa gtgaatgtca acggcggggc    2640
catcgcgctc gggcatccta tcggtgccag tggtgctcgt attctggtca cactattaca    2700
tgccatgcag gcacgcgata aaacgctggg gctggcaaca ctgtgcattg gcggcggtca    2760
gggaattgcg atggtgattg aacggttgaa ttgaggatct tgaattaagg aggacagcta    2820
aatgacaata ggtatcgata aaataaactt ttacgttcca agtactatg tagacatggc      2880 taaattagca gaagcacgcc aagtagaccc aaacaaattt ttaattggaa ttggtcaaac    2940
tgaaatggct gttagtcctg taaaccaaga catcgtttca atgggcgcta acgctgctaa    3000
ggacattata acagacgaag acaaaagaa aattggtatg gtaattgtgg caactgaatc     3060
agcagttgat gctgctaaag cagccgctgt tcaaattcac aacttattag gtattcaacc    3120
ttttgcacgc tgctttgaaa tgaaagaagc ttgttatgct gcaacaccag caattcaatt    3180
agctaaagat tatttagcaa ctagaccgaa tgaaaagta ttagttattg ctacagatac      3240
agcacgttat ggattgaact caggcggcga gccaacacaa ggtgctggcg cagttgcgat    3300
ggttattgca cataatccaa gcatttggc attaaatgaa gatgctgttg cttacactga      3360
agacgtttat gatttctggc gtccaactgg acataaatat ccattagttg atggtgcatt    3420
atctaaagat gcttatatcc gctcattcca acaaagctgg aatgaatacg caaaacgtca    3480
aggtaagtcg ctagctgact tcgcatctct atgcttccat gttccatta caaaaatggg      3540 taaaaaggca ttagagtcaa tcattgataa cgctgatgaa acaactcaag agcgtttacg    3600
ttcaggatat gaagatgctg tagattataa ccgttatgtc ggtaatattt atactggatc     3660
attatattta agcctaatat cattacttga aaatcgagat ttacaagctg gtgaaacaat    3720
cggtttattc agttatggct caggttcagt tggtgaattt tatagtgcga cattagttga    3780
aggctacaaa gatcatttag atcaagctgc acataaagca ttattaaata accgtactga    3840
agtatctgtt gatgcatatg aaacattctt caaacgtttt gatgacgttg aatttgacga    3900
agaacaagat gctgttcatg aagatcgtca tattttctac ttatcaaata ttgaaaataa    3960
cgttcgcgaa tatcacagac cagagtaatt aggatctatt caggaaacag accatgtcca    4020
tgcaaagttt agataagaat tttcgacatt tatctcgtaa agaaagtta caacaattgg      4080 ttgataagca atggttatca gaagaacaat tcgacatttt actgaatcat ccattaatcg    4140
atgaagaagt agccaatagt ttaattgaaa atgtcatcgc gcaaggtgca ttacccgttg    4200
gattattacc gaatatcatt gtggacgata aggcatatgt tgtacctatg atggtggaag    4260
agccttcagt tgtcgctgca gctagttatg gtgcaaagct agtgaatcag actggcggat    4320
ttaaaacggt atcttctgaa cgtattatga taggtcaaat cgtctttgat ggcgttgacg    4380
atactgaaaa attatcagca gacattaaag ctttagaaaa gcaaattcat aaaattgcgg    4440
atgaggcata tccttctatt aaagcgcgtg gtggtggtta ccaacgtata gcgattgata    4500
catttcctga gcaacagtta ctatctttaa aagtatttgt tgatacgaaa gatgctatgg    4560
gcgctaatat gctaatacg attttagagg ccataactgc attttaaaa aatgaatttc      4620 cgcaaagcga cattttaatg agtatttat ccaatcatgc aacagcgtcc gttgttaaag      4680
```

```
ttcaaggcga aattgatgtt aaagatttag caaggggcga gagaactgga gaagaggttg    4740
ccaaacgaat ggaacgtgct tctgtattgg cccaagtaga tattcatcgt gcagcaacac    4800
ataataaagg tgttatgaat ggcatacatg ctgttgtttt agcaacagga aatgatacgc    4860
gtggtgcaga agcaagtgcg catgcatacg cgagtcgtga cggacagtat cgtggtattg    4920
ctacatggcg ttacgatcaa gatcgtcaac gattgattgg tacaattgaa gtgcctatga    4980
cattggcaat cgttggcggt ggtacaaaag tattaccaat tgctaaagct tcattagagc    5040
tactaaatgt agagtcagca caagaattag gtcatgtagt tgctgccgtt ggtttagcgc    5100
aaaactttgc agcatgtcgc gcgcttgtgt cagaaggtat tcaacaaggt catatgagtt    5160
tacaatataa atcattagct atcgttgtag gggcaaaagg tgatgaaatt gctaaagtag    5220
ctgaagcttt gaaaaaagaa ccccgtgcaa atacacaagc agcggaacat attttacaag    5280
aaattagaca acaataagga tcttttttaag gatctccagg catcaaataa aacgaaaggc    5340
tcagtcgaaa gactgggcct ttcgttttat ctgttgtttg tcggtgaacg ctctctacta    5400
gagtcacact ggctcacctt cgggtgggcc tttctgcgtt tatagcgaat tgatctggtt    5460
tgacagctta tcatcgactg cacggtgcac caatgcttct ggcgtcaggc agccatcgga    5520
agctgtggta tggctgtgca ggtcgtaaat cactgcataa ttcgtgtcgc tcaaggcgca    5580
ctcccgttct ggataatgtt ttttgcgccg acatcataac ggttctggca aatattctga    5640
aatgagctgt tgacaattaa tcatccggct cgtataatgt gtggaattgt gagcggataa    5700
caatttcagg atctaggagg aaataaccat gtctctgcca ttcctgacgt ctgcgccagg    5760
taaggtgatc atcttcggcg agcactctgc ggtgtacaat aagccggccg tcgccgcctc    5820
tgtgtctgcg ttacgcacct acctgctgat cagcgaatct tctgcaccgg acacgatcga    5880
gctggacttt ccggacatca gcttcaacca caagtggagc atcaacgact tcaacgcgat    5940
cacggaggac caggtgaaca gccaaaagct ggccaaagcc cagcaagcaa ccgacggtct    6000
gtctcaggag ctggtgtctc tgctggaccc gctgttagcg cagttaagcg agagcttcca    6060
ttaccacgcc gcgttctgct tcctgtacat gttcgtttgc ctgtgcccgc acgcaaagaa    6120
catcaagttc agcctgaaga gcacgctgcc gattggcgca ggcttaggct ctagcgcatc    6180
tatcagcgtg agcctggcgc tggcgatggc ctatctgggt ggcctgattg cagcaacga    6240 cctggagaaa ctgagcgaaa cgacaagca catcgtgaac cagtgggcct ttatcggcga    6300
gaagtgcatt catggcaccc cgagcggcat tgacaacgca gttgccacgt atggcaacgc    6360
cctgctgttc gagaaagaca gccacaacgg cacgatcaac acgaacaact tcaagttcct    6420
ggacgacttc ccggcgatcc cgatgattct gacctacacc cgtatcccac gcagcaccaa    6480
ggatttagtc gcccgcgtgc gtgttttagt caccgaaaag ttcccggagg tgatgaagcc    6540
gatcctggac gcgatgggcg agtgcgcgct gcagggtctg gagatcatga ccaagctgag    6600
caagtgcaag gcaccgacg atgaggcggt ggagaccaac aatgagctgt acgagcagct    6660
gctggagctg atccgtatca atcacggcct gctggtctct atcggtgtgt ctcacccggg    6720
cctggaactg atcaaaaacc tgagcgacga cctgcgcatt ggctctacga aattaacggg    6780
tgcaggtggc ggtggctgct ctttaacgct gctgcgccgt gacattacgc aggagcaaat    6840
cgacagcttc aagaagaagc tgcaggacga cttcagctac gagacgttcg agacggacct    6900
gggcggcacg ggctgttgcc tgctgagcgc caaaaatctg aacaaggacc tgaagatcaa    6960
aagcctggtg ttccagctgt tcgaaaacaa gacgaccacg aagcagcaga tcgacgacct    7020
```

```
gttactgccg ggtaacacca atctgccgtg gacgtcttaa ggatctagga gggagatcat   7080
atgagcgaat tacgtgcatt cagcgcgcca ggtaaggcac tgctggccgg tggctacctg   7140
gtgttagaca ccaagtacga ggcgttcgtc gtcggcttat ctgcccgtat gcatgcagtt   7200
gcccacccgt atggtagcct gcagggctct gacaagttcg aagtgcgtgt gaagagcaag   7260
cagttcaagg acggcgagtg gctgtaccac attagcccaa agagcggctt catcccggtt   7320
agcattggtg gcagcaagaa cccatttatc gagaaggtca ttgccaacgt cttcagctac   7380
ttcaagccga atatggacga ttactgcaac cgcaacctgt tcgtcatcga cattttcagc   7440
gacgacgcgt accacagcca agaggactct gttacggagc atcgtggtaa ccgccgcctg   7500
agcttccaca gccatcgcat tgaggaggtg ccgaagacgg gtctgggttc tagcgccggt   7560
ttagttaccg tcttaacgac ggcgttagcg agcttcttcg tgagcgacct ggagaacaac   7620
gtggacaagt accgcgaagt gattcataac ctggcgcagg tggcacattg tcaggcccaa   7680
ggtaagattg gctctggttt tgatgtggca gcggccgcct atggctctat ccgctatcgc   7740
cgctttccgc cggccctgat cagcaatctg ccggacatcg gctctgcgac gtatggtagc   7800
aaactggcgc atctggtgga cgaagaagac tggaacatca ccattaagtc taatcacctg   7860
ccgagcggct taacgttatg gatgggcgat atcaagaacg gcagcgaaac ggttaagctg   7920
gtgcagaaag tgaaaaactg gtacgacagc cacatgccgg aaagcctgaa gatttacacg   7980
gagctggacc acgccaatag ccgtttcatg gatggtctga gcaagctgga ccgcctgcac   8040
gaaacccacg acgactacag cgaccaaatc ttcgagagcc tggagcgcaa tgactgcacc   8100
tgccagaagt acccggagat cacggaggtc cgcgatgccg tggcaacgat tcgccgtagc   8160
ttccgcaaaa ttacgaagga gagcggcgcg gatatcgaac caccggtcca gacgtctctg   8220
ctggacgact gtcaaacctt aaagggcgtg ttaacgtgcc tgattccggg cgcgggtggt   8280
tacgacgcca ttgccgtcat cacgaaacag gacgtcgatc tgcgcgcaca aacggccaac   8340
gacaaacgtt tcagcaaagt ccaatggctg gatgttacgc aggccgactg gggtgttcgc   8400
aaggagaagg acccggaaac gtatctggat aagtgaggat ctaggaggat tatgagatga   8460
ccgtttacac agcatccgtt accgcacccg tcaacatcgc aacccttaag tattggggga   8520
aaagggacac gaagttgaat ctgcccacca attcgtccat atcagtgact ttatcgcaag   8580
atgacctcag aacgttgacc tctgcggcta ctgcacctga gtttgaacgc gacactttgt   8640
ggttaaatgg agaaccacac agcatcgaca tgaaagaac tcaaaattgt ctgcgcgacc   8700
tacgccaatt aagaaaggaa atggaatcga aggacgcctc attgcccaca ttatctcaat   8760
ggaaactcca cattgtctcc gaaaataact ttcctacagc agctggttta gcttcctccg   8820
ctgctggctt tgctgcattg gtctctgcaa ttgctaagtt ataccaatta ccacagtcaa   8880
cttcagaaat atctagaata gcaagaaagg ggtctggttc agcttgtaga tcgttgtttg   8940
gcggatacgt ggcctgggaa atgggaaaag ctgaagatgg tcatgattcc atggcagtac   9000
aaatcgcaga cagctctgac tggcctcaga tgaaagcttg tgtcctagtt gtcagcgata   9060
ttaaaaagga tgtgagttcc actcagggta tgcaattgac cgtggcaacc tccgaactat   9120
ttaaagaaag aattgaacat gtcgtaccaa agagatttga agtcatgcgt aaagccattg   9180
ttgaaaaaga tttcgccacc tttgcaaagg aaacaatgat ggattccaac tctttccatg   9240
ccacatgttt ggactctttc cctccaatat tctacatgaa tgacacttcc aagcgtatca   9300
tcagttggtg ccacaccatt aatcagtttt acggagaaac aatcgttgca tacacgtttg   9360
atgcaggtcc aaatgctgtg ttgtactact tagctgaaaa tgagtcgaaa ctctttgcat   9420
```

```
ttatctataa attgtttggc tctgttcctg gatgggacaa gaaatttact actgagcagc    9480
ttgaggcttt caaccatcaa tttgaatcat ctaactttac tgcacgtgaa ttggatcttg    9540
agttgcaaaa ggatgttgcc agagtgattt taactcaagt cggttcaggc ccacaagaaa    9600
caaacgaatc tttgattgac gcaaagactg gtctaccaaa ggaataagga tctaggaggt    9660
aatgataatg caaacggaac acgtcatttt attgaatgca cagggagttc ccacgggtac    9720
gctgaaaaag tatgccgcac acacggcaga cacccgctta catctcgcgt tctccagttg    9780
gctgtttaat gccaaaggac aattattagt tacccgccgc gcactgagca aaaaagcatg    9840
gcctggcgtg tggactaact cggtttgtgg gcacccacaa ctgggagaaa gcaacgaaga    9900
cgcagtgatc cgccgttgcc gttatgagct tggcgtggaa attacgcctc ctgaatctat    9960
ctatcctgac tttcgctacc cgccaccga tccgagtggc attgtggaaa atgaagtgtg   10020
tccggtattt gccgcacgca ccactagtgc gttacagatc aatgatgatg aagtgatgga   10080
ttatcaatgg tgtgatttag cagatgtatt acacggtatt gatgccacgc cgtgggcgtt   10140
cagtccgtgg atggtgatgc aggcgacaaa tcgcgaagcc agaaaacgat tatctgcatt   10200
tacccagctt aaataaggat ctcgcaaaaa accccgcttc ggcggggttt tttcgccgac   10260
tgcacggtgc accaatgctt ctggcgtcag gcagccatcg gaagctgtgg tatggctgtg   10320
caggtcgtaa atcactgcat aattcgtgtc gctcaaggcg cactcccgtt ctggataatg   10380
ttttttgcgc cgacatcata acggttctgg caaatattct gaaatgagct gttgacaatt   10440
aatcatccgg ctcgtataat gtgtggaatt gtgagcggat aacaatttca ggatctttta   10500
agaaggagat atacatggaa tttgacttca caaatacat ggactccaaa gcgatgacgg   10560
taaatgaagc actgaacaaa gcgatccctc tgcgttatcc gcagaaaatc tacgaaagca   10620
tgcgttacag cctgctggca ggcggcaagc gtgttcgtcc ggttctgtgt attgccgcat   10680
gtgaactggt aggtggtacc gaagaactgg cgatcccgac cgcgtgcgca attgaaatga   10740
tccacacgat gtccctgatg cacgatgatc tgccgtgtat cgacaacgac gatctgcgtc   10800
gcggtaaacc gactaaccac aaaattttcg gtgaggatac cgcagtgact gctggtaacg   10860
cactgcactc ttacgccttc gagcatatcg cggtttctac ttctaaaacc gttggtgctg   10920
accgcatcct cgtatggtg tccgagctgg tcgtgctac tggctctgaa ggtgttatgg   10980
gtggtcagat ggtagacatc gcatccgaag gcgatccgtc tatcgacctg cagaccctgg   11040
aatggattca catccacaaa accgcaatgc tgctggaatg ctccgttgtt tgcggtgcaa   11100
tcattggcgg tgccagcgaa atcgtaatcg aacgtgcccg tcgctacgcc cgctgtgttg   11160
gtctgctgtt ccaggtagtt gatgacattc tggacgtaac taaaagcagc gacgaactgg   11220
gtaagactgc gggcaaggac ctgatctctg ataaagccac ctacccaaag ctgatgggtc   11280
tggaaaaggc caaggagttc tccgatgaac tgctgaaccg tgcgaagggt gaactgtcct   11340
gcttcgaccc agttaaagcc gctccgctgc tgggcctggc agactacgtg gcatttcgtc   11400
agaattaagg atcttttaag aaggagatat actaaggatc caaactcgag taaggatctc   11460
caggcatcaa ataaaacgaa aggctcagtc gaaagactgg gcctttcgtt ttatctgttg   11520
tttgtcggtg aacgctctct actagagtca cactggctca ccttcgggtg gcctttctg   11580 cgtttatacc tagggatata ttccgcttcc tcgctcactg actcgctacg ctcggtcgtt   11640
cgactgcggc gagcggaaat ggcttacgaa cggggcggag atttcctgga agatgccagg   11700
aagatactta acagggaagt gagagggccg cggcaaagcc gtttttccat aggctccgcc   11760
```

```
cccctgacaa gcatcacgaa atctgacgct caaatcagtg gtggcgaaac ccgacaggac    11820
tataaagata ccaggcgttt ccccctggcg gctccctcgt gcgctctcct gttcctgcct    11880
ttcggtttac cggtgtcatt ccgctgttat ggccgcgttt gtctcattcc acgcctgaca    11940
ctcagttccg ggtaggcagt tcgctccaag ctggactgta tgcacgaacc ccccgttcag    12000
tccgaccgct gcgccttatc cggtaactat cgtcttgagt ccaacccgga aagacatgca    12060
aaagcaccac tggcagcagc cactggtaat tgatttagag gagttagtct tgaagtcatg    12120
cgccggttaa ggctaaactg aaaggacaag ttttggtgac tgcgctcctc caagccagtt    12180
acctcggttc aaagagttgg tagctcagag aaccttcgaa aaaccgccct gcaaggcggt    12240
tttttcgttt tcagagcaag agattacgcg cagaccaaaa cgatctcaag aagatcatct    12300
tattaatcag ataaaatatt tctagatttc agtgcaattt atctcttcaa atgtagcacc    12360
tgaagtcagc cccatacgat ataagttgtt actagtgctt ggattctcac caataaaaaa    12420
cgcccggcgg caaccgagcg ttctgaacaa atccagatgg agttctgagg tcattactgg    12480
atctatcaac aggagtccaa gcgagctcga tatcaaatta cgccccgccc tgccactcat    12540
cgcagtactg ttgtaattca ttaagcattc tgccgacatg gaagccatca caaacggcat    12600
gatgaacctg aatcgccagc ggcatcagca ccttgtcgcc ttgcgtataa tatttgccca    12660
tggtgaaaac gggggcgaag aagttgtcca tattggccac gtttaaatca aaactggtga    12720
aactcaccca gggattggct gagacgaaaa acatattctc aataaaccct ttagggaaat    12780
aggccaggtt ttcaccgtaa cacgccacat cttgcgaata tatgtgtaga aactgccgga    12840
aatcgtcgtg gtattcactc cagagcgatg aaaacgtttc agtttgctca tggaaaacgg    12900
tgtaacaagg gtgaacacta tcccatatca ccagctcacc gtctttcatt gccatacgaa    12960
attccggatg agcattcatc aggcgggcaa gaatgtgaat aaaggccgga taaaacttgt    13020
gcttattttt ctttacggtc tttaaaaagg ccgtaatatc cagctgaacg gtctggttat    13080
aggtacattg agcaactgac tgaaatgcct caaaatgttc tttacgatgc cattgggata    13140
tatcaacggt ggtatatcca gtgatttttt tctccatttt agcttcctta gctcctgaaa    13200
atctcgataa ctcaaaaaat acgcccggta gtgatcttat ttcattatgg tgaaagttgg    13260
aacctcttac gtgccgatca acgtctcatt ttcgccagat atc                     13303

<210> SEQ ID NO 12
<211> LENGTH: 45
<212> TYPE: DNA
<213> ORGANISM: Artificial sequence
<220> FEATURE:
<223> OTHER INFORMATION: Marker

<400> SEQUENCE: 12
gcggccaacg atgaaaacta ttctgaaaac tatgcggatg cgtct                    45
```